(12) United States Patent
Hatakeyama et al.

(10) Patent No.: US 8,183,058 B2
(45) Date of Patent: May 22, 2012

(54) TARGET SUBSTANCE DETECTION ELEMENT, TARGET SUBSTANCE DETECTION METHOD, AND METHOD FOR PRODUCING TARGET SUBSTANCE DETECTION ELEMENT

(75) Inventors: Satoru Hatakeyama, Kawasaki (JP); Takashi Ikeda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 210 days.

(21) Appl. No.: 12/524,348

(22) PCT Filed: Mar. 17, 2008

(86) PCT No.: PCT/JP2008/055605
§ 371 (c)(1),
(2), (4) Date: Jul. 23, 2009

(87) PCT Pub. No.: WO2008/126664
PCT Pub. Date: Oct. 23, 2008

(65) Prior Publication Data
US 2010/0047928 A1 Feb. 25, 2010

(30) Foreign Application Priority Data
Mar. 22, 2007 (JP) ................................ 2007-074857

(51) Int. Cl.
*G01N 33/543* (2006.01)
(52) U.S. Cl. ........ 436/518; 422/408; 422/420; 422/421; 422/425; 435/287.2; 435/287.7; 435/287.8; 435/287.9; 435/970; 436/514; 436/807
(58) Field of Classification Search ........................ None
See application file for complete search history.

(56) References Cited

U.S. PATENT DOCUMENTS
7,387,901 B2 6/2008 Nishiuma et al.
(Continued)

FOREIGN PATENT DOCUMENTS
JP 6-3317 A 1/1994
(Continued)

OTHER PUBLICATIONS

PCT International Search Report and Written Opinion of the International Searching Authority, Mailing Date Jul. 24, 2008.
(Continued)

*Primary Examiner* — Chris L Chin
(74) *Attorney, Agent, or Firm* — Fitzpatrick, Cella, Harper & Scinto

(57) ABSTRACT

It is intended to provide a target substance detection element wherein a target substance capturing body for capturing target substances is immobilized with good orientation in a desired region on the surface of the target substance detection element, a method for producing the target substance detection element, and a detection method using the target substance detection element. The present invention provides a target substance detection element for detecting the presence or absence or concentration of a target substance in a sample, characterized in that: the target substance detection element includes at least a detection substrate including plural layers and a target substance capturing body immobilized on the surface of the detection substrate; the target substance capturing body has at least a first peptide region specifically recognizing a first layer of the plural layers constituting the detection substrate and binding to the first layer and a second peptide region specifically recognizing a second layer different from the first layer of the plural layers and binding to the second layer; and the first layer and the second layer are adjacent to each other.

5 Claims, 9 Drawing Sheets

U.S. PATENT DOCUMENTS

| | | | |
|---|---|---|---|
| 2003/0073104 A1 | 4/2003 | Belcher et al. |
| 2005/0106625 A1 | 5/2005 | Woodbury et al. |
| 2005/0130258 A1 | 6/2005 | Trent et al. |
| 2006/0286142 A1 | 12/2006 | Woodbury et al. |
| 2007/0178522 A1 | 8/2007 | Shiotsuka et al. |
| 2007/0231926 A1 | 10/2007 | Ikeda |
| 2007/0237673 A1 | 10/2007 | Ikeda et al. |
| 2007/0298510 A1 | 12/2007 | Imamura et al. |
| 2008/0187461 A1 | 8/2008 | Hatakeyama et al. |
| 2008/0225292 A1 | 9/2008 | Nishiuma et al. |
| 2008/0241964 A1 | 10/2008 | Kaieda et al. |
| 2008/0268497 A1 | 10/2008 | Hashimoto et al. |
| 2008/0309323 A1 | 12/2008 | Okano et al. |
| 2009/0000360 A1 | 1/2009 | Ogawa et al. |
| 2009/0021250 A1 | 1/2009 | Ikeda |
| 2009/0042317 A1 | 2/2009 | Ikeda |
| 2009/0170220 A1 | 7/2009 | Shiotsuka et al. |
| 2009/0215197 A1 | 8/2009 | Shiotsuka et al. |

FOREIGN PATENT DOCUMENTS

| | | |
|---|---|---|
| JP | 2005-95154 A | 4/2005 |
| JP | 2005-312446 A | 11/2005 |
| JP | 2006-145400 A | 6/2006 |
| JP | 2006-234762 A | 9/2006 |
| WO | 2005/016971 A1 | 2/2005 |

OTHER PUBLICATIONS

Hendji, et al., "Covalent immobilization of glucose oxidase on silanized platinum microelectrode for the monitoring of glucose", Sensors and Actuators, vol. B15-16, 1993, pp. 127-134.

Kim, et al., "Patterned Arrays of Au Rings for Localized Surface Plasmon Resonance", Langmuir, vol. 22, 2006, pp. 7109-7112.

Liu, et al., Effect of probe geometry on the Hall response in an inhomogeneous magnetic field: A numerical study, Journal of Applied Physics, vol. 83, No. 11, Jun. 1, 1998, pp. 6161-6165.

Scott, et al., "Searching for Peptide Ligands with an Epitope Library", Science, vol. 249, 1990, pp. 386-390.

Cwirla, et al., "Peptides on phage: A vast library of peptides for identifying ligands", Proceedings of the National Academy of Sciences, vol. 87, Aug. 1990, pp. 6378-6382.

Sarikaya, et al., Molecular biomimetics: nanotechnology through biology, Nature, vol. 2, Sep. 2003, pp. 577-585.

Halling, et al., "Magnetic supports for immobilized enzymes and bioaffinity adsorbents", Enzyme Microb. Technol., vol. 2, Jan. 1980, pp. 2-10.

Sambrook, et al., Molecular Cloning, A Laboratory Manual, Second Edition, Cold Spring Harbor Laboratory Press, 1989, p. 5.72.

Brown, et al., "Protein-Mediated Particle Assembly", Nano Letters, vol. 1, No. 7, 2001, pp. 391-394.

Whaley, et al., "Selection of peptides with semiconductor binding specificity for directed nanocrystal assembly", Nature, vol. 405, Jun. 2000, pp. 665-668.

Francisco, et al., "Production and fluorescence-activated cell sorting of *Escherichia coli* expressing a functional antibody fragment on the external surface", Proceedings of the National Academy of Sciences, vol. 90, Nov. 1993, pp. 10444-10448.

Pistor, et al., "Expression of Viral Hemagglutinin on the Surface of *E. coli*", Klin Wochenschr, vol. 66, 1988, pp. 110-116.

Fuchs, et al., "Targeting Recombinant Antibodies to the Surface of *Escherichia Coli*: Fusion to a Peptidoglycan Associated Lipoprotein", Bio/Technology, vol. 9, Dec. 1991, pp. 1369-1372.

Charbit, et al., "Versatility of a vector for expressing foreign polypeptides at the surface of Gram-negative bacteria", Gene, vol. 70, 1988, pp. 181-189.

Bradbury, et al., "Use of Living Columns to Select Specific Phage Antibodies", Bio/Technology, vol. 11, Dec. 1993, pp. 1565-1569.

Hedegaard, et al., "Type 1 fimbriae of *Escherichia coli* as carriers of heterologous antigenic sequences", Gene, vol. 85, 1989, pp. 115-124.

Hofnung, "Expression of Foreign Polypeptides at the *Escherichia coli* Cell Surface", Methods in Cell Biology, vol. 34, 1991, pp. 77-105.

Klauser, et al., "Extracellular transport of cholera toxin B subunit using Neisseria IgA protease β-domain: conformation-dependent outer membrane translocation", EMBO Journal, vol. 9, 1990, pp. 1991-1999.

Sinha, et al., "Differences in Electrostatic Properties at Antibody-Antigen Binding Sites: Implications for Specificity and Cross-Reactivity", Biophysical Journal, vol. 83, Dec. 2002, pp. 2946-2968.

Hao, et al., "Synthesis and Optical Properties of Anisotropic Metal Nanoparticles", Journal of Fluorescence, vol. 14, No. 4, Jul. 2004, pp. 331-341.

Lapicki, et al., "Functionalization of Micro-Hall Effect Sensors for Biomedical Applications Utilizing Superparamagnetic Beads", IEEE Transactions on Magnetics, vol. 41, No. 10, Oct. 2005, pp. 4134-4136.

U.S. Appl. No. 11/645,028, filed Dec. 26, 2006, Hatakeyama.

FIG. 3
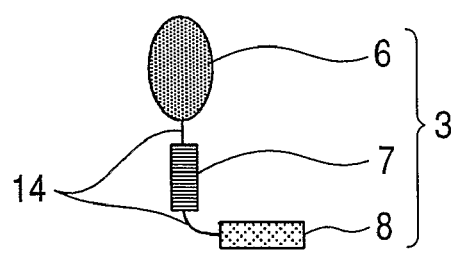
(A)
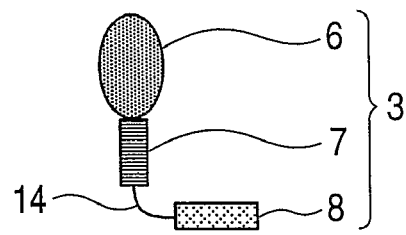
(D)
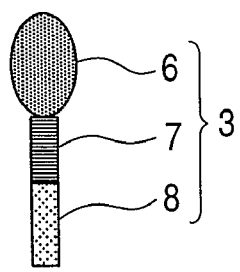
(B)
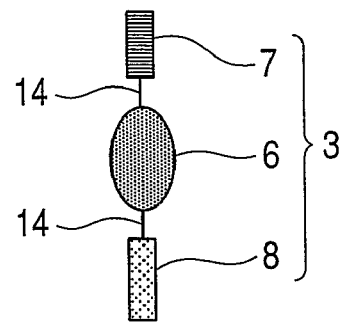
(E)
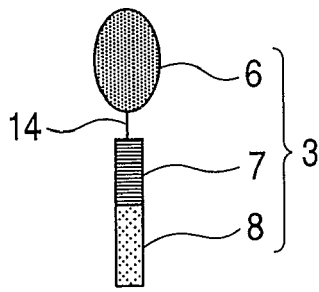
(C)
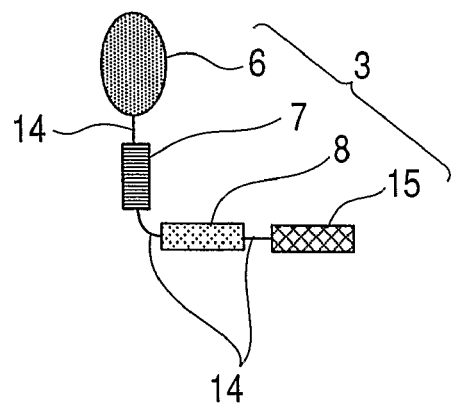
(F)

FIG. 5

```
          10          20          30          40          50          60
GATATCGTCCTGACCCAGAGCCCGGCGACCCTCTCGGTCACCCCCGGCAACTCGGTGTCC
 D  I  V  L  T  Q  S  P  A  T  L  S  V  T  P  G  N  S  V  S 70          80          90         100         110         120
CTCTCGTGCCGCGCCTCGCAGTCGATCGGCAACAACCTCCACTGGTATCAGCAGAAGTCG
 L  S  C  R  A  S  Q  S  I  G  N  N  L  H  W  Y  Q  Q  K  S 130         140         150         160         170         180
CACGAGAGCCCGCGCCTCCTGATCAAGTACGCCAGCCAGTCGATCTCGGGGATCCCGTCG
 H  E  S  P  R  L  L  I  K  Y  A  S  Q  S  I  S  G  I  P  S 190         200         210         220         230         240
CGCTTCAGCGGCTCGGGCTCGGGCACCGACTTCACCCTGTCGATCAACAGCGTCGAGACG
 R  F  S  G  S  G  S  G  T  D  F  T  L  S  I  N  S  V  E  T 250         260         270         280         290         300
GAGGACTTCGGCATGTACTTCTGCCAGCAGTCGAACAGCTGGCCGTACACCTTCGGCGGC
 E  D  F  G  M  Y  F  C  Q  Q  S  N  S  W  P  Y  T  F  G  G 310         320         330         340         350         360
GGTACCAAGCTGGAGATCACCGCGGGCGGGGGCGGTAGCGGCGGTGGCGGGTCGGGCGGT
 G  T  K  L  E  I  T  A  G  G  G  G  S  G  G  G  G  S  G  G 370         380         390         400         410         420
GGCGGATCGGATATCCAGCTGCAGGAGTCGGGCCCGAGCCTCGTCAAGCCGTCGCAGACC
 G  G  S  D  I  Q  L  Q  E  S  G  P  S  L  V  K  P  S  Q  T 430         440         450         460         470         480
CTGTCGCTCACCTGCAGCGTCACCGGCGACTCGATCACCTCGGACTACTGGTCGTGGATC
 L  S  L  T  C  S  V  T  G  D  S  I  T  S  D  Y  W  S  W  I 490         500         510         520         530         540
CGCAAGTTCCCCGGCAACCGCCTCGAGTACATGGGCTACGTCAGCTACTCGGGCAGCACC
 R  K  F  P  G  N  R  L  E  Y  M  G  Y  V  S  Y  S  G  S  T 550         560         570         580         590         600
TACTACAACCCCTCGCTGAAGAGCCGCATCTCGATCACCCGCGACACCTCCAAGAACCAG
 Y  Y  N  P  S  L  K  S  R  I  S  I  T  R  D  T  S  K  N  Q
```

FIG. 6

```
          610        620        630        640        650        660
TACTACCTGGACCTCAACTCGGTCACCACCGAGGACACCGCCACCTACTACTGCGCGAAC
 Y  Y  L  D  L  N  S  V  T  T  E  D  T  A  T  Y  Y  C  A  N 670        680        690        700        710        720
TGGGACGGCGACTACTGGGGCCAGGGCACCCTCGTCACCGTCTCCGCCGCGGGCGGGGGC
 W  D  G  D  Y  W  G  Q  G  T  L  V  T  V  S  A  A  G  G 730        740        750        760        770        780
GGTAGCGGCGGTGGCGGGTCGGGCGGTGGCGGATCGATGCACGGCAAAACCCAGGCGACC
 G  S  G  G  G  S  G  G  G  S  M  H  G  K  T  Q  A  T 790        800        810        820        830        840
TCAGGTACCATTCAGAGCATGCACGGTAAAACCCAGGCGACTTCAGGTACCATCCAGTCT
 S  G  T  I  Q  S  M  H  G  K  T  Q  A  T  S  G  T  I  Q  S 850        860        870        880        890        900
ATGCATGGCAAAACCCAGGCGACTTCTGGTACCATTCAGTCTATGCATTCAGCTAGCGGC
 M  H  G  K  T  Q  A  T  S  G  T  I  Q  S  M  H  S  A  S  G 910        920        930        940        950        960
TCGGGCGGCGGCGGCTCTGGTGGTGGTTCTGGTGGCGGCTCTGAGGGTGGCGGCTCTGAG
 S  G  G  G  G  S  G  G  G  S  G  G  G  S  E  G  G  G  S  E 970        980        990       1000       1010       1020
GGAGGCGGTTCCGGTGGTGGCTCTGGTTCTATTCCGATGCATGTGCATCACAAACACCCG
 G  G  G  S  G  G  G  S  G  S  I  P  M  H  V  H  H  K  H  P 1030       1040       1050       1060       1070
CATGTTATCCCGATGCATGTGCACCATAAACACCCGCACGTG
 H  V  I  P  M  H  V  H  H  K  H  P  H  V
```

FIG. 7A
GOLD-BINDING PEPTIDE REGION SEQUENCE

M H G K T Q A T S G T I Q S M H G K T Q A T S G T I Q S M
H G K T Q A T S G T I Q S M H

FIG. 7B
SiO$_2$-BINDING PEPTIDE REGION SEQUENCE

I P M H V H H K H P H V I P M H V H H K H P H V

FIG. 7C
(G4S)3 LINKER SEQUENCE

G G G G S G G G G S G G G G S

FIG. 7D
LINKER SEQUENCE BETWEEN MATERIAL-BINDING PEPTIDES

S A S G S G G G G S G G G S G G G S E G G G S E G G G
S G G G S G S

CROSS-SECTION OF MAGNETIC
FIELD DETECTION REGION

TARGET SUBSTANCE DETECTION ELEMENT, TARGET SUBSTANCE DETECTION METHOD, AND METHOD FOR PRODUCING TARGET SUBSTANCE DETECTION ELEMENT

TECHNICAL FIELD

The present invention relates to a target substance detection element, a target substance detection method, and a method for producing a target substance detection element.

BACKGROUND ART

So-called biosensors utilize molecular recognition abilities possessed by biological substances. Such biologic substances include nucleic acid molecules including genes (e.g., DNA and RNA), aptamers, sugar-binding proteins, enzymes, and antibodies. Many researches and developments have been conducted on the biosensors with the aim of extensive application thereof.

With the increased interest in environmental pollutant problems, social safety, and health, further technical developments have been demanded increasingly for biosensors. The goal thereof is, for example, to apply these biosensors to diverse targets to be detected.

Specifically, detection apparatuses have been developed widely using the selectivity of molecular recognition possessed by each biological substance molecule, as described above. Examples thereof include DNA sensor chips. These DNA sensor chips utilize the nucleotide sequence-dependent complementary hydrogen bond between deoxyribonucleic acid (hereinafter, referred to as DNA) chains (hybridization reaction between complementary chains) Alternative examples thereof include antibody sensors or protein chips. These apparatuses utilize molecular recognition abilities derived from the specific binding abilities between protein molecules and low-molecular-weight compounds or between protein molecules. For example, the apparatuses utilize antigen-antibody reaction or sugar-lectin binding to detect disease markers or the like eluted into blood. Further examples thereof include the developments of detection apparatuses based on a variety of detection approaches, including biosensors such as enzyme sensors. The enzyme sensors utilize oxidoreductase or hydrolase to detect substrate substance concentrations. These biosensors are typified by glucose sensors for diabetes mellitus patients.

Current biosensors utilizing these biological substances generally adopt a system using the form of a biological substance-immobilized base substance. In this system, the biological substances used (e.g., nucleic acid molecules such as DNA or proteins such as antibodies or enzymes) are immobilized on the surface of a base substance such as a substrate or carrier.

Alternatively, one example of performance qualities required for biosensors currently under development includes high sensitivity and size reduction. The important technical challenge to this goal of "high sensitivity and size reduction" is to effectively use the space of a very small reaction field or detection field and to enhance detection sensitivity. The aim of size reduction is to reduce the amounts of samples collected from patients so as to ease the burden on the patients. As a result, techniques have been demanded which are capable of detecting, with high sensitivity, target molecules present in very small amounts of samples.

Examples of methods for immobilizing biological substances, particularly, proteins, on a substrate include an approach which involves: forming a coating layer of a protein solution on substrate surface; then removing the solvent contained in the coating layer; and drying the substrate so as to immobilize the proteins on the substrate surface through physical adsorption. Alternative examples thereof include an approach which involves: for the purpose of introducing reactive functional groups, chemically modifying substrate surface or protein molecules; and then forming a chemical bond using the reaction between the introduced reactive functional groups so as to immobilize the protein molecules on the substrate surface through chemical bonds. An alternative previously known approach is the immobilization of proteins onto substrate surface using molecular recognition.

Patent Document 1 discloses one example of an immobilization method based on physical adsorption. This document discusses a method for producing an enzyme electrode. This method utilizes an approach which involves immobilizing enzyme proteins through physical adsorption on the surface of a conductive substrate via an organic charge-transfer complex layer formed on the conductive substrate surface.

Non-Patent Document 1 discloses one example of an immobilization method using a chemical bond. This document discusses an immobilization method which involves forming, using a cross-linking agent, the chemical bond between an amino group derived from an amine-based silane coupling agent provided on the platinum-deposited surface of a silicon substrate and a peptide chain. In addition, detection apparatuses such as biosensors obtained by immobilizing antibodies onto a glass substrate may be prepared using such an immobilization method. In this case, reactive functional groups are introduced into the surface of a glass substrate by treatment with a silane coupling agent. Then, peptide chains are immobilized thereon via a chemical bond using a cross-linking agent.

Patent Document 2 discloses one example of an immobilization method using molecular recognition. This document discusses a technique of specifically immobilizing proteins with orientation onto a substrate through molecular recognition abilities imparted by fusing the proteins with affinity peptides having affinity for silicon oxide arranged on the substrate surface. This method can maintain the maximum target substance-binding abilities of the proteins.

While immobilization techniques have made progress, detection techniques for increasing the added value of biosensors have been developed acceleratingly. For example, the non-labeling detection of target substances provides reduction in the number of detection steps, reduction in time, and kinetic analysis. For the purpose of further achieving detection with high sensitivity or low-molecular-weight compound detection, the development of biosensors has been attempted using a localized surface plasmon resonance (hereinafter, referred to as LSPR) phenomenon.

Non-Patent Document 3 discloses the detection of biotin-avidin biological reaction using an LSPR element. In this LSPR element, nano-order metal structures (rings and dots) are arranged on substrate surface. Alternatively, Non-Patent Document 4 has attempted the development of more effective sensors. In this document, LSPR elements having various shapes are evaluated for electric field strength distribution by calculation. Alternatively, techniques of applying Hall elements to biosensors have also been known. The Hall elements, one of semiconductor magnetic sensors, utilize the Hall effects. The aim of the techniques is to basically quantitatively detect, with ultra-high sensitivity, target substances labeled with magnetic substances (Non-Patent Document 2 and Patent Document 3). Moreover, Non-Patent Document 5 discusses more effective sensors. In this document, positions within magnetically sensitive surface, Hall voltages, and magnetic flux density distribution are evaluated by calculation.

Alternatively, Patent Document 4 discloses one example of a reaction promotion method. This document discusses a technique of detecting biomolecular interaction in a short time in real time. In this technique, the dielectrophoresis of biomolecules is induced by applying a high-frequency alternating voltage thereto. As a result, very small amounts of target substances are concentrated so as to promote the reaction.

However, such a detection technique or reaction promotion method basically has inhomogeneous distribution, such as a gradient of electric field or magnetic field strength, in a sensing or reaction promotion region. Therefore, the conventional techniques of immobilizing biological substances onto these regions are not necessarily optimized in terms of quantitative detection or the like. The important challenge to the increase of the added value of biosensors can be to develop more effective techniques of immobilizing biological substances. Specifically, protein immobilization techniques have been demanded which are more precise or effective, particularly, as the whole biosensor involving a detection unit or reaction promotion unit, in addition to orientational or homogeneous immobilization techniques, such as the conventional immobilization techniques.

Patent Document 1: Japanese Patent Application Laid-Open No. 06-003317
Patent Document 2: Japanese Patent Application Laid-Open No. 2005-95154
Patent Document 3: Japanese Patent Application Laid-Open No. 2006-234762
Patent Document 4: Japanese Patent Application Laid-Open No. 2006-145400
Non-Patent Document 1: Sensors and Actuators B 15-16 p127 (1993)
Non-Patent Document 2: IEEE TRANSACTIONS ON MAGNETICS, VOL. 41, NO. 10, October 2005
Non-Patent Document 3: Langmuir 2006, 22, 7109-7112
Non-Patent Document 4: Journal of Fluorescence Vol. 14 No. 4 (2004)
Non-Patent Document 5: Journal of Applied Physics Vol. 83 No. 11 (1998) p 6161-p 6165

DISCLOSURE OF THE INVENTION

The protein immobilization techniques described above focus on almost homogeneously immobilizing proteins onto a sensing or reaction promotion region and imparting orientation to immobilized biological substances. On the other hand, these techniques may have the uneven distribution of electric field or magnetic field strength within a reaction region. In such a case, target substance capturing bodies are almost homogeneously immobilized on the sensor member or its neighborhood region. Therefore, obtained signals vary depending on the position of the interaction between the target substance capturing bodies and target substances. In other words, variation in signal per reacted target substance may result, leading to reduction in sensitivity. Likewise, variation in signal per magnetic substance may result depending on the acting position of the magnetic substance-labeled target substances described above in a sensing region, leading to unsuccessful quantitative detection.

In other words, target substance capturing bodies to be immobilized on a substrate may not achieve immobilization in a desired region with controlled orientation suitable for their applications. This presents an obstacle to enhanced precision in terms of detection sensitivity and quantitative performance. Therefore, for obtaining desired detection sensitivity appropriate to the amount of target substance capturing bodies immobilized, the amount of samples must be increased. Alternatively, for achieving greater functionality such as, quantitative performance, some action must be taken. For example, a sensor region itself is increased in size, and target substance capturing bodies are analogously immobilized in a desired region. The area of a substrate on which target substance capturing bodies are immobilized may be widen excessively. This presents a big obstacle to the size reduction of an apparatus itself. Moreover, high cost required for the production or an increased usage also including-biological substance materials with low contribution to sensing that are immobilized in regions other than the desired one causes increases in cost as the whole apparatus. This presents a big obstacle to the reduction of necessary cost per step. In addition, the increased amount of samples places a burden on patients.

Thus, protein immobilization techniques have been demanded which are capable of immobilizing target substance capturing bodies to be immobilized on a substrate, in a desired region with controlled orientation suitable for their applications. Particularly, protein immobilization techniques have been demanded which are more precise or effective as the whole biosensor apparatus suitable for detection or reaction promotion techniques.

Accordingly, an object of the present invention is to provide a target substance detection element wherein a target substance capturing body for capturing target substances is immobilized with good orientation in a desired region on the surface of the target substance detection element, a method for producing the target substance detection element, and a detection method using the target substance detection element.

The present invention relates to
a target substance detection element for detecting the presence or absence or concentration of a target substance in a sample, characterized in that:
the target substance detection element comprises at least a detection substrate and a target substance capturing body immobilized on the surface of the detection substrate;
the detection substrate has a first layer including a portion of the surface of the detection substrate and a second layer including a portion of the surface of the detection substrate and being different from the first layer;
the first layer and the second layer are made of different materials;
the target substance capturing body has at least a first peptide region specifically recognizing the first layer and binding to the first layer and a second peptide region specifically recognizing the second layer and binding to the second layer; and
the first layer and the second layer are adjacent to each other.

According to an alternative aspect, the present invention relates to
a method for producing a target substance detection element, characterized by comprising:
preparing a detection substrate having, on the surface, at least a portion of a first layer and of a second layer made of a material different from that of the first layer;
preparing a target substance capturing body having a first peptide region specifically recognizing the first layer and binding to the first layer and a second peptide region specifically recognizing the second layer and binding to the second layer, the second layer being different from the first layer and being made of a material different from that of the first layer;

bringing the target substance capturing body into contact with the detection substrate so as to bind the first peptide region of the target substance capturing body to the first layer and the second peptide region of the target substance capturing body to the second layer of the detection substrate; and removing the target substance capturing body that has specifically recognized only one of the first layer and the second layer and bound to the one of the first layer and the second layer, by utilizing the difference in binding strength between the target substance capturing body that has specifically recognized at least both of the first layer and the second layer and bound to both of the first layer and the second layer and the target substance capturing body that has specifically recognized only one of the first layer and the second layer and bound to the one of the first layer and the second layer.

According to an alternative aspect, the present invention relates to a target substance detection method for detecting the presence or absence or concentration of a target substance in a sample, characterized by comprising:

bringing a sample into contact with a target substance detection element comprising at least a detection substrate and a target substance capturing body immobilized on the surface of the detection substrate; and obtaining a signal from the target substance detection element, wherein:

the detection substrate has, on the surface, at least a portion of a first layer and of a second layer made of a material different from that of the first layer;

the target substance capturing body of the target substance detection element has a first peptide region specifically recognizing the first layer and binding to the first layer and a second peptide region specifically recognizing the second layer and binding to the second layer; and the first layer and the second layer are adjacent to each other.

The target substance capturing body can have a linker having one or more amino acid(s) between the first peptide region and the second peptide region.

The first peptide region and the second peptide region can have different amino acid sequences.

The first layer can be a detection part.

According to an alternative aspect, the present invention relates to a target substance detection element for detecting the presence or absence or concentration of a target substance in a sample, characterized in that:

the target substance detection element comprises at least a detection substrate comprising plural layers and a target substance capturing body immobilized on the surface of the detection substrate;

the target substance capturing body has at least a first peptide region specifically recognizing a first layer of the plural layers constituting the detection substrate and binding to the first layer and a second peptide region specifically recognizing a second layer different from the first layer of the plural layers and binding to the second layer; and the first layer and the second layer are adjacent to each other.

According to an alternative aspect, the present invention relates to a method for producing a target substance detection element, characterized by comprising:

preparing a target substance capturing body having a first peptide region specifically recognizing a first layer of plural layers constituting a detection substrate and binding to the first layer and a second peptide region specifically recognizing a second layer different from the first layer of the plural layers and binding to the second layer;

bringing the target substance capturing body into contact with the detection substrate so as to bind the first peptide region of the target substance capturing body to the first layer of the detection substrate and the second peptide region of the target substance capturing body to the second layer of the detection substrate; and removing the target substance capturing body that has specifically recognized only one of the first layer and the second layer and bound to the one of the first layer and the second layer, by utilizing the difference in binding strength between the target substance capturing body that has specifically recognized at least both of the first layer and the second layer and bound to both of the first layer and the second layer and the target substance capturing body that has specifically recognized only one of the first layer and the second layer and bound to the one of the first layer and the second layer.

According to an alternative aspect, the present invention relates to a target substance detection method for detecting the presence or absence or concentration of a target substance in a sample, characterized by comprising:

bringing a sample into contact with a target substance detection element comprising at least a detection substrate comprising plural layers and a target substance capturing body immobilized on the surface of the detection substrate; and obtaining a signal from the target substance detection element, wherein:

the target substance capturing body of the target substance detection element has a first peptide region specifically recognizing a first layer of the plural layers constituting the detection substrate and binding to the first layer and a second peptide region specifically recognizing a second layer different from the first layer of the plural layers and binding to the second layer; and the first layer and the second layer are adjacent to each other.

The use of the present invention can provide a target substance detection element wherein target substance capturing bodies are immobilized with good orientation at a desired position on the surface, and a method for producing the target substance detection element.

Further features of the present invention will become apparent from the following description of exemplary embodiments with reference to the attached drawings.

(A), (B), (C), (D), (E) and (F) in FIG. 3 are schematic diagrams illustrating examples of the constitution of target substance capturing bodies used in the target substance detection element of the present invention.

Figure 4:
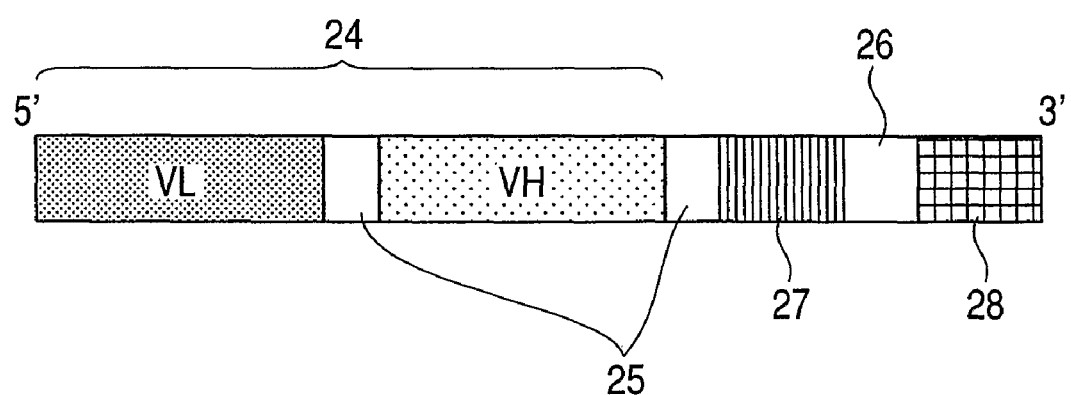

FIG. 4 is a schematic diagram illustrating the arrangement of functional regions in a target substance capturing body used in the target substance detection element of the present invention.

FIG. 5 is a diagram illustrating the sequence (first half) of a fusion of the arranged functional regions in the target substance capturing body illustrated in FIG. 4.

FIG. 6 is a diagram showing a continuation (latter half) of the sequence of the fusion of FIG. 5.

FIGS. 7A, 7B, 7C and 7D illustrate one example of a target substance capturing body sequence used in the target substance detection element of the present invention.

Figure 8:
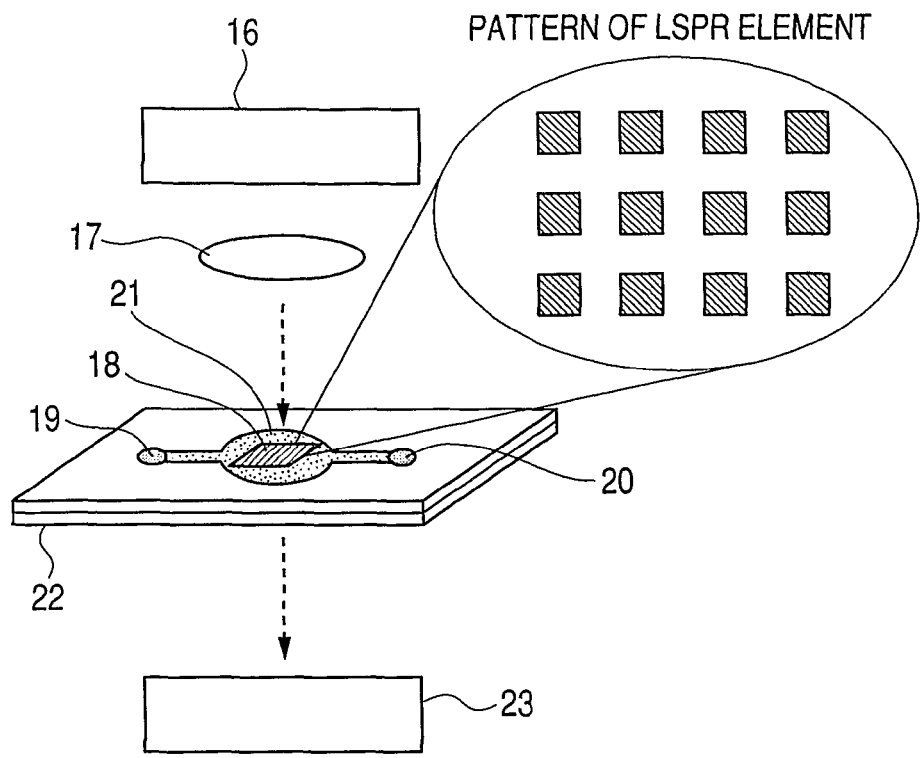

FIG. 8 is a diagram illustrating the outlined structure of a detection apparatus with an LSPR element used in Example 3.

Figure 9:
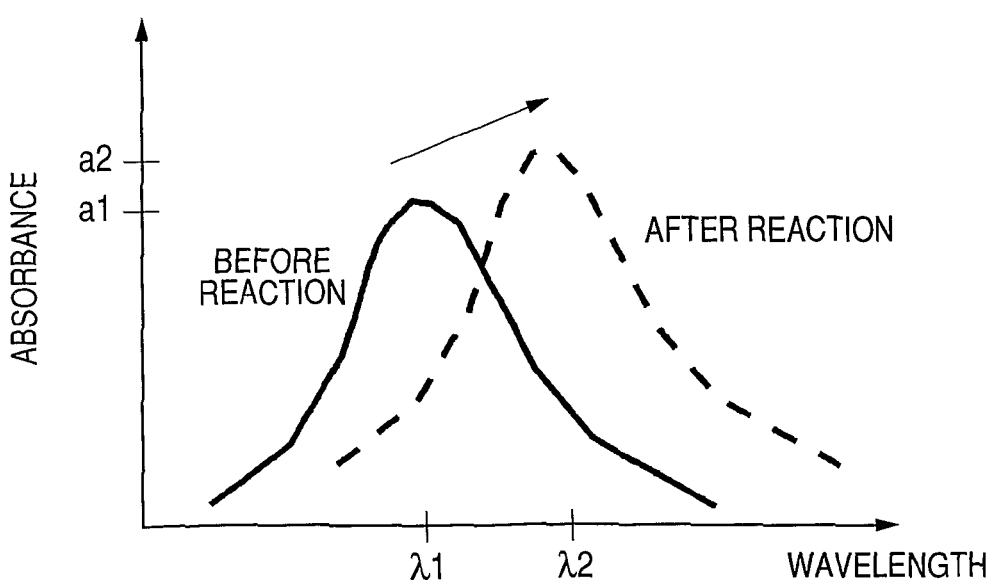

FIG. 9 is a graph in which the absorption spectrum of a gold structure of Example 3 is compared between before and after reaction.

Figure 10:
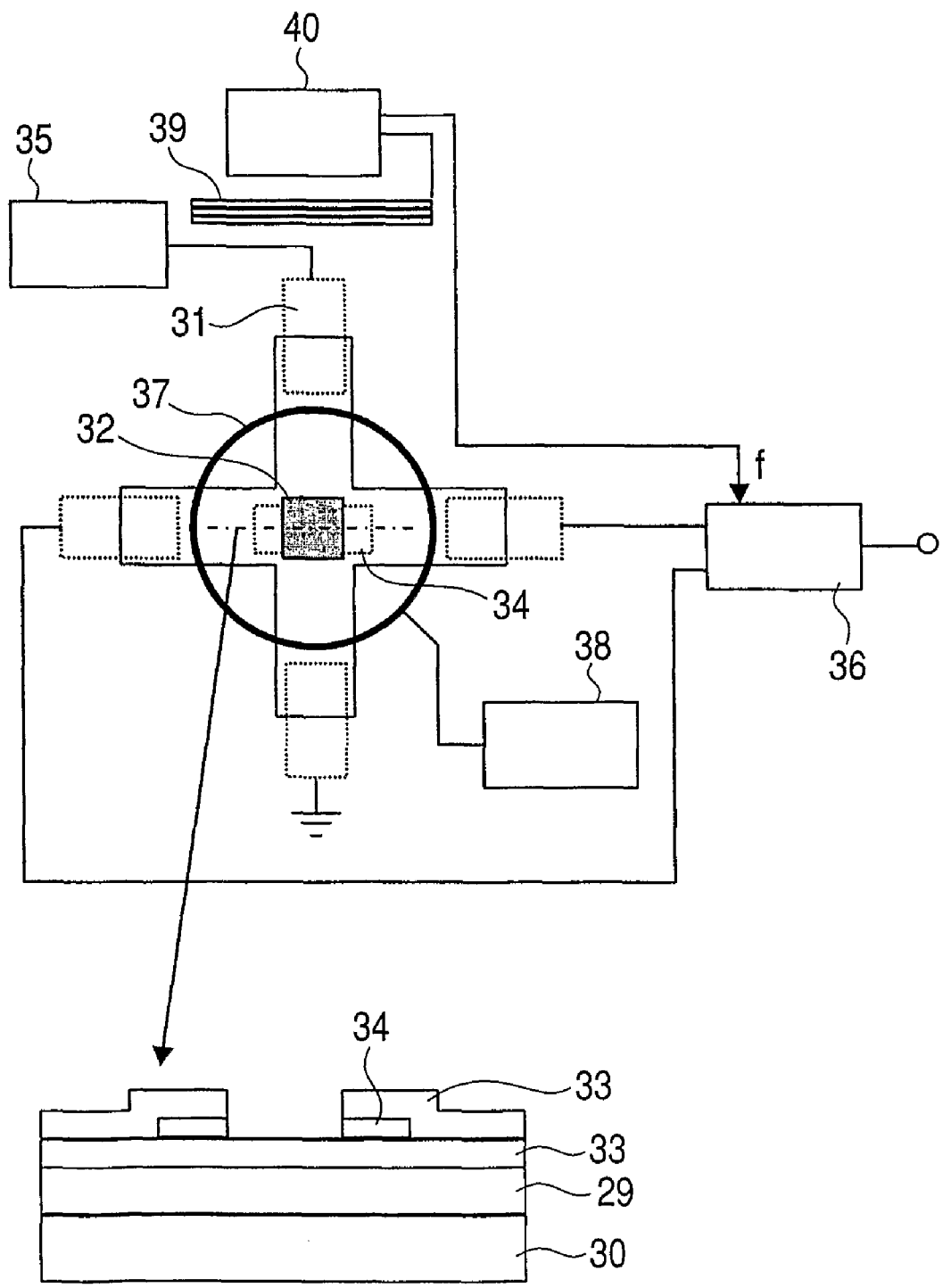

FIG. 10 is a diagram illustrating the structure of a Hall sensor of Example 4 and a detection circuit.

BEST MODES FOR CARRYING OUT THE INVENTION

Hereinafter, the present invention will be described more specifically.
(Target Substance Detection Element)

A target substance detection element of the present invention is a target substance detection element for detecting the presence or absence or concentration of a target substance in a sample. The target substance detection element includes at least a detection substrate including plural layers including a first layer and a second layer and a target substance capturing body immobilized on the surface of the detection substrate. The target substance capturing body has at least a first peptide region specifically recognizing a first layer of the plural layers constituting the detection substrate and binding to the first layer and a second peptide region specifically recognizing a second layer different from the first layer and binding to the second layer. The target substance detection element is characterized in that the first layer and the second layer are adjacent to each other. In this context, the second layer different from the first layer means that a material constituting the first layer and a material constituting the second layer are different from each other. For example, molecules or atoms constituting the first layer and molecules or atoms constituting the second layer are different from each other.

Figure 1:
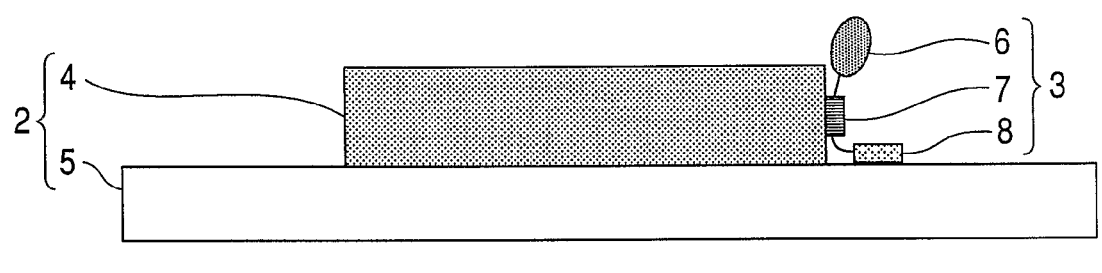
FIG. 1 is a schematic diagram illustrating one example of the constitution of a detection substrate used in the target substance detection element of the present invention.

FIG. 1 illustrates one example of the target substance detection element of the present invention.

A target substance detection element 1 has a detection substrate 2 and a target substance capturing body 3. The detection substrate 2 has a first layer 4 and a second layer 5 adjacent to the first layer. The target substance capturing body 3 has a target substance capturing site 6, a first peptide region 7, and a second peptide region 8.

The first peptide region 7 of the target substance capturing body 3 specifically recognizes the first layer 4 of the detection substrate 2 and binds to the first layer 4. The second peptide region 8 of the target substance capturing body 3 specifically recognizes the second layer 5 of the detection substrate and binds to the second layer 5. In this context, the phrase "specifically recognizing and binding" used in the present invention means that this binding can be differentiated from non-specific adsorption/binding. In other words, the binding powers of the peptide regions to the materials of interest have dissociation constants ($K_D$) two or more times smaller than those of their non-specific adsorption/binding powers to other materials constituting the detection substrate. These dissociation constants can be an order of magnitude smaller than those of their non-specific adsorption/binding powers. Particularly, each peptide region can have a dissociation constant ($K_D$) of $1 \times 10^{-4}$ M or smaller at room temperature under buffer conditions in the presence of 0.1% Tween 20. This binding of interest can be differentiated from the non-specific adsorption. Alternatively, the whole target substance capturing body may satisfy an apparent $K_D$ value two or more times smaller than the dissociation constant ($K_D$) of each peptide region, as a result of the action of each peptide region. This apparent $K_D$ value can be an order of magnitude smaller than the dissociation constant ($K_D$) of each peptide region. Particularly, the target substance capturing body can have a dissociation constant ($K_D$) of $1 \times 10^{-6}$ M or smaller at room temperature under buffer conditions in the presence of 0.1% Tween 20. This difference in $K_D$ permits the removal of non-specifically adsorbed molecules by utilizing the difference in binding strength. Thus, the object can be achieved. Furthermore, such a target substance capturing body having a dissociation constant ($K_D$) Of $1 \times 10^{-6}$ M or smaller can sufficiently function as an anchor molecule for immobilization.

In this way, the target substance capturing body 3 can be arranged in the neighborhood of the boundary between the first layer 4 and the second layer 5 constituting the detection substrate 2. Moreover, the target substance capturing body 3 can be arranged with good orientation only at the desired position (in the neighborhood of the boundary between the first layer 4 and the second layer 5). In this context, the neighborhood falls within 500 nm in consideration of the relationship between a target substance capturing body size and an inhomogeneous distribution region. The neighborhood can fall within 100 nm and can particularly fall within 20 nm. Such arrangement permits the immobilization of the target substance capturing body, for example, only onto parts with strong magnetic field strength, even in the presence of inhomogeneous distribution of magnetic field strength used in detection. More specifically, LSPR elements have been known to have good detection sensitivity at the ends of a metal structure. Therefore, the target substance capturing body 3 can be arranged only at the ends of a metal structure to obtain an LSPR element with good sensitivity.

Figure 2A:
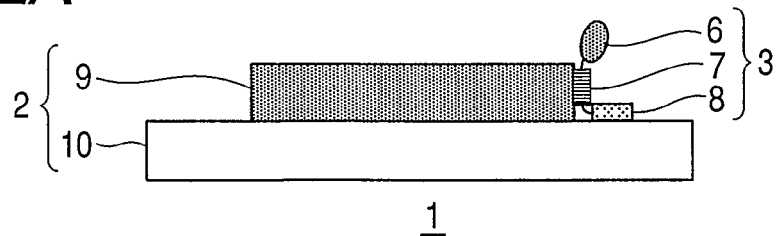
FIGS. 2A, 2B, 2C, 2D and 2E are schematic diagrams illustrating one example of the constitution of a detection substrate used in the target substance detection element of the present invention.
Figure 2B:
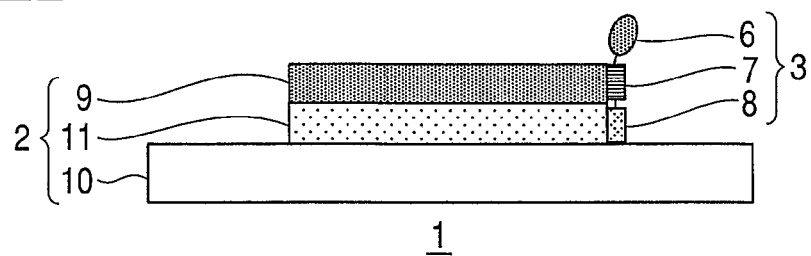
Figure 2C:
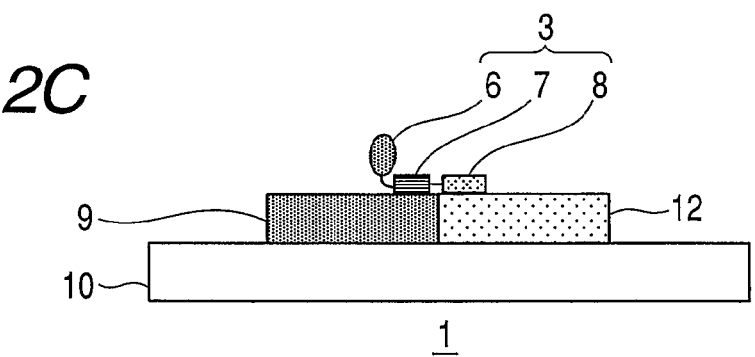

The first layer 4 and the second layer 5 constitute the detection substrate and may be any layer as long as the first layer and the second layer are adjacent to each other. For example, as illustrated in FIG. 2A, a detection substrate may include a base material 10 and a detection part 9 present on the surface of the base material 10. In this case, the detection part 9 serves as a first layer, and the base material 10 serves as a second layer. Alternatively, as illustrated in FIG. 2B, a detection substrate that can be used may include a base material 10, a detection part 9 present on the base material 10, and an intermediate layer 11 present between the base material 10 and the detection part 9. In this case, the detection part 9 serves as a first layer, and the intermediate layer 11 serves as a second layer. Alternatively, as illustrated in FIG. 2C, a detection substrate may include a base material 10, a detection part 9 present on the surface of the base material 10, and a blocking layer 12. In this case, the detection part 9 serves as a first layer, and the blocking layer 12 serves as a second layer. Alternatively, the detection part may not be a first layer. Such a detection substrate is illustrated in, for example, FIG. 2D. This detection substrate includes a base material 10, a detection part 9 present on the surface of the base material 10, and a blocking layer 12 present on the surface of the detection part. In this case, the blocking layer 12 serves as a first layer, and the base material 10 serves as a second layer. Alternatively, a detection substrate illustrated in FIG. 2E may be used. This detection substrate includes a base material 10, a detection part 9 present on the surface of the base material 10, a blocking layer 12 present on the surface of the detection part 9, and a layer 13 present on the surface of the blocking layer 12. In this case, the layer 13 serves as a first layer and the blocking layer 12 serves as a second layer. In this context, the phrase "the first layer and the second layer are adjacent to each other" used in the present invention means that "the first layer and the second layer are present in contact with each other at their boundaries". However, an extremely thin layer, such as an adhesive layer, different from the first layer and the second layer may be present between the first layer and the second layer. The phrase "the first layer and the second layer are adjacent to each other" also encompasses such a constitution. In this context, the phrase "extremely thin" means a thickness of 50 nm or smaller.

Hereinafter, each part constituting the detection substrate will be described.

The detection substrate includes plural layers having at least a first layer and a second layer. Moreover, the detection substrate has a detection part for detecting target substances. In this context, the detection part may be a first layer or may be a second layer, as described above. Alternatively, the detection part may be present as an additional part different from the first layer and the second layer. In this context, the term "layer" means one of plural parts constituted in contact with each other. Thus, the layer here is not limited to a flat membrane-like form and also conceptually encompasses patterns, such as dots, formed on the base material. Moreover, the layer is not limited to those in which the maximum length (B) in the direction perpendicular to the base material within the layer is shorter than the maximum length (A) in the direction parallel to the base material. The layer also encompasses those in which the maximum length (B) is equal to or larger than the maximum length (A).

A material constituting the detection part may be any material used in sensing (detection) using physical or chemical phenomena such as LSPR or Hall effects. For example, for detection using LSPR, metals, for example, gold (Au), silver (Ag), and titanium (Ti), can be used in the detection part. Alternatively, for magnetic detection (e.g., Hall element detection), semiconductors, for example, silicon (Si), germanium (Ge), gallium arsenide (GaAs), indium arsenide (InAs), and indium antimonide (InSb), can be used as a material constituting the detection part.

Examples of materials constituting layers other than the detection part, of the plural layers of the detection substrate include materials including any one or more selected from metals, metal oxide, inorganic semiconductors, organic semiconductors, glasses, ceramics, natural polymers, synthetic polymers, and plastics or including a complex thereof. Examples of such materials that can be used include, but not limited to, base substance materials disclosed in Japanese Patent Application Laid-Open No. 2005-312446. Moreover, the base material can assume a shape such as plate-like, particulate, porous, protrusion, fibrous, cylindrical, reticular forms. Moreover, the base material may have a size variously selected according to use applications.

In this context, the base material functions as a support for supporting the whole detection substrate. Thus, a layer, for example, the detection part, other than the base material constituting the detection substrate may function as a support. In such a case, the base material does not have to be present.

Figure 2D:
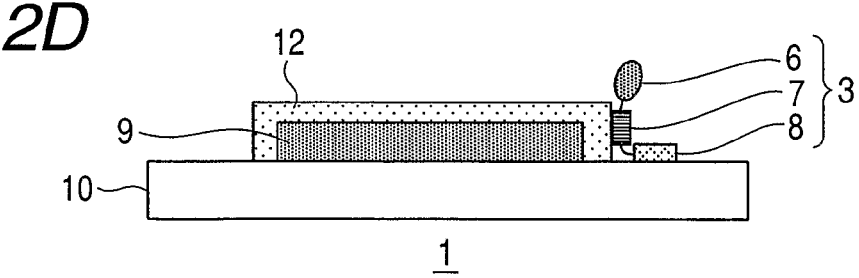
Figure 2E:
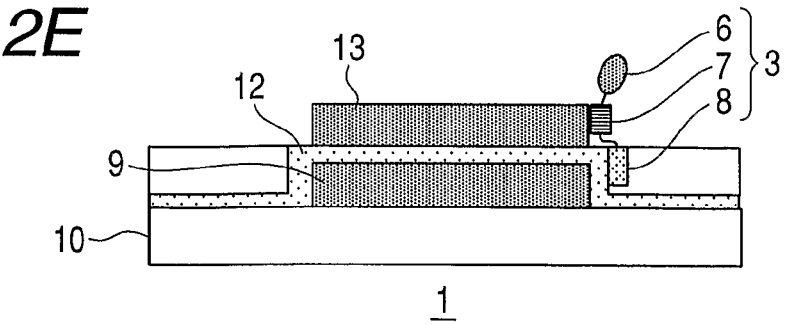

Alternatively, the plural layers constituting the detection substrate, as illustrated in FIGS. 2C to 2E, may have a blocking layer having the ability to inhibit the non-specific adsorption of target substances. In such a case, a material having hydrophilic functional groups can be used in the blocking layer 12. Examples of such a material include proteins (e.g., BSA (bovine serum albumin) and caseins) having the ability to prevent non-specific adsorption, organic polymers such as PEG (polyethylene glycol), and hydrophilic polymers. Alternatively, as illustrated in FIGS. 2D and 2E, the detection part surface may be coated with the blocking layer 12. In such a case, a water-resistant material can be used in the blocking layer 12. As a result, the blocking layer 12 has the function of preventing a non-specific adsorption of target substances and can additionally have the function of enhancing water resistance for a detection part weakly resistant to water. For a detection substrate with no blocking layer, a surfactant or the like can be added into a sample solution.

For forming the detection part on the base material surface, for example, patterning using photolithography or etching techniques can be performed.

Next, the target substance capturing body will be described.

(Target Substance Capturing Body)

The target substance capturing body may be any substance that has the first peptide region and the second peptide region and can capture target substances.

(A) to (F) in FIG. 3 respectively illustrate one example of the target substance capturing body.

As illustrated in FIG. 3, a target substance capturing body 3 includes: a first peptide region 7 specifically recognizing the first layer 4 of the detection substrate and binding to the first layer 4; a second peptide region 8 specifically recognizing the second layer 5 different from the first layer 4 of the detection substrate and capturing the second layer 5; and a target substance capturing site 6.

In this context, the first peptide region has a structure having an amino acid sequence. The first peptide region may be formed by any of primary, secondary, and tertiary structures specifically recognizing the first layer and binding thereto. For example, the first peptide region may be formed by a region localized in a tertiary structure such as β sheet. In such a case, the amino acid sequence constituting the first peptide region may have a discontinuous primary structure. Likewise, the second peptide region may be formed by any of primary, secondary, and tertiary structures specifically recognizing the second layer and binding thereto. The amino acid sequence constituting the first peptide region and the amino acid sequence constituting the second peptide region are different sequences.

In (A) in FIG. 3, the target substance capturing body has a target substance capturing site 6, a first peptide region 7, and a second peptide region 8 in this order from top to bottom. Linkers 14 establish the bond between the target substance capturing site 6 and the first peptide region 7 and between the first peptide region 7 and the second peptide region 8. On the other hand, as illustrated (E) in FIG. 3, a target substance capturing site 6 is present between a first peptide region 7 and a second peptide region 8. Linkers 14 may establish the bond between these parts. Alternatively, the linkers can be present between parts. However, as illustrated (B), (C), and (D) in FIG. 3, some parts may be bound directly. Furthermore, as illustrated (F) in FIG. 3, the layers constituting the detection substrate may include a third layer different from the layers (first and second layers) specifically recognized and bound by the first peptide region 7 and the second peptide region 8, and a third peptide region 15 recognizing this third layer and binding thereto may be present. The linkers 14 that establish the bond between parts may be the same or may be different.

(Target Substance)

Target substances to be detected by the target substance detection element of the present invention are broadly classified into non-biological substances and biological substances.

Specific examples of the non-biological substances include environmental pollutants such as PCBs differing in the number and position of chlorine substitution, dioxins also differing in the number and position of chlorine substitution, and endocrine disrupting chemicals (e.g., so-called environmental hormones). Examples of the endocrine disrupting chemicals include hexachlorobenzene, pentachlorophenol, 2,4,5-trichloroacetic acid, 2,4-dichlorophenoxyacetic acid, amitrole, atrazine, alachlor, hexachlorocyclohexane, ethyl parathion, chlordane, oxychlordane, nonachlor, 1,2-dibromo-3-chloropropane, DDT, Kelthane, aldrin, endrin, dieldrin, endosulfan (benzoepin), heptachlor, heptachlor epoxide, malathion, methomyl, methoxychlor, mirex, nitrofen, toxaphene, trifluralin, alkyl phenol (5 to 9 carbon atoms), nonyl phenol, octylnonyl phenol, 4-octyl phenol, bisphenol A, di-2-ethylhexyl phthalate, butyl benzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitrotoluene, octachlorostyrene, aldicarb, benomyl, Kepone (chlordecone), manzeb (mancozeb), maneb, metiram, metribuzin, cypermethrin, esfenvalerate, fenvalerate, permethrin, vinclozolin, zineb, ziram, dipentyl phthalate, dihexyl phthalate, and dipropyl phthalate.

These pollutants that exhibit unfavorable effects in vivo are incorporated into various organs, tissues, and cells via proteins (e.g., receptor proteins produced by cells in vivo) exhibiting binding abilities to the pollutants or via nucleic acid molecules having complex formation abilities with the pollutants. Thus, these pollutants can be detected using these proteins exhibiting binding abilities to the pollutants or nucleic acid molecules having complex formation abilities with the pollutants as organic substances in the biological substance-immobilized sensor element according to the present invention.

Examples of the biological substances to be detected include biological substances selected from nucleic acids, proteins, sugar chains, lipids, and complexes thereof. More specifically, the biological substances encompass biomolecules selected from nucleic acids, proteins, sugar chains, and lipids. Specifically, samples containing substances selected from DNA, RNA, aptamers, genes, chromosomes, cell membranes, viruses, antigens, antibodies, lectin, haptens, hormones, receptors, enzymes, peptides, glycosphingo, and sphingolipids can be detected. Furthermore, bacteria or cells themselves that produce the "biological substances" may also be included in the broad sense in the "target substances" as long as a detection method according to the present invention is applied to the detection of the "biological substances" derived from the bacteria or cells.

Specific examples of the proteins include so-called disease markers. Examples of the disease marker proteins include: α-fetoprotein (AFP), an acid glycoprotein produced in hepatic cells for a fetal period and present in fetal blood, which serves as a marker for hepatocellular carcinoma (primary liver cancer), hepatoblastoma, metastatic liver cancer, and yolk sac tumor; PIVKA-II, abnormal prothrombin appearing during hepatic parenchymal injury, which is confirmed to specifically appear in hepatocellular carcinoma; BCA225, a glycoprotein that is an antigen immunohistochemically specific for breast cancer, which serves as a marker for advanced primary breast cancer and recurrent/metastatic breast cancer; basic fetoprotein (BFP), a basic fetal protein found in extracts from human fetal serum, intestine and brain tissue, which serves as a marker for ovarian cancer, testicular tumor, prostatic cancer, pancreatic carcinoma, biliary tract carcinoma, hepatocellular carcinoma, renal cancer, lung cancer, gastric cancer, bladder carcinoma, and colon cancer; CA15-3, a carbohydrate antigen, which serves as a marker for advanced breast cancer, recurrent breast cancer, primary breast cancer, and ovarian cancer; CA19-9, a carbohydrate antigen, which serves as a marker for pancreatic carcinoma, biliary tract carcinoma, gastric cancer, liver cancer, colon cancer, and ovarian cancer; CA72-4, a carbohydrate antigen, which serves as a marker for ovarian cancer, breast cancer, colorectal cancer, gastric cancer, and pancreatic carcinoma; CA125, a carbohydrate antigen, which serves as a marker for ovarian cancer (particularly, serous cystadenocarcinoma), adenocarcinoma of the uterine body, cancer of the Fallopian tube, adenocarcinoma of the uterine cervix, pancreatic carcinoma, lung cancer, and colon cancer; CA130, a glycoprotein, which serves as a marker for epithelial ovarian cancer, cancer of the Fallopian tube, lung cancer, hepatocellular carcinoma, and pancreatic carcinoma; CA602, a core protein antigen, which serves as a marker for ovarian cancer (particularly, serous cystadenocarcinoma), adenocarcinoma of the uterine body, and adenocarcinoma of the uterine cervix; CA54/61 (CA546), a core carbohydrate-related antigen, which serves as a marker for ovarian cancer (particularly, mucinous cystadenocarcinoma), adenocarcinoma of the uterine cervix, and adenocarcinoma of the uterine body; carcinoembryonic antigen (CEA), which has currently been used most widely for assistance in diagnosing cancer as a marker antigen associated with tumors such as colon cancer, gastric cancer, rectal cancer, biliary tract carcinoma, pancreatic carcinoma, lung cancer, breast cancer, uterine cancer, and urinary system cancer; DUPAN-2, a carbohydrate antigen, which serves as a marker for pancreatic carcinoma, biliary tract carcinoma, hepatocellular carcinoma, gastric cancer, ovarian cancer, and colon cancer; elastase 1, an exocrine pancreatic protease present in the pancreas and specifically hydrolyzing elastic fiber elastin (composing arterial walls, tendons, etc.) in connective tissues, which serves as a marker for pancreatic carcinoma, cystic carcinoma of the pancreas, and biliary tract carcinoma; immunosuppressive acidic protein (IAP), a glycoprotein present at high concentrations in the ascites and serum of human patients with cancer, which serves as a marker for lung cancer, leukemia, cancer of the esophagus, pancreatic carcinoma, ovarian cancer, renal cancer, cholangioma, gastric cancer, bladder carcinoma, colon cancer, thyroid carcinoma, and malignant lymphoma; NCC-ST-439, a carbohydrate antigen, which serves as a marker for pancreatic carcinoma, biliary tract carcinoma, breast cancer, colon cancer, hepatocellular carcinoma, adenocarcinoma of the lung, and gastric cancer; γ-seminoprotein (γ-Sm), a glycoprotein, which serves as a marker for prostatic cancer; prostate-specific antigen (PSA), a glycoprotein extracted from human prostate tissues and present only in prostate tissues, which thus serves as a marker for prostatic cancer; prostatic acid phosphatase (PAP), an enzyme secreted from the prostate and hydrolyzing phosphoric ester at acidic pH, which is used as a tumor marker for prostatic cancer; neuron-specific enolase (NSE), a glycolytic enzyme specifically present in nervous tissues and neuroendocrine cells, which serves as a marker for lung cancer (particularly, small cell carcinoma of the lung), neuroblastoma, nervous system tumor, islet cell cancer, small cell carcinoma of the esophagus, gastric cancer, renal cancer, and breast cancer; squamous cell carcinoma-related antigen (SCC antigen), a protein extracted and purified from the hepatic metastatic foci of squamous cell carcinoma of the uterine cervix, which serves as a marker for uterine cancer (cervical squamous cell carcinoma), lung cancer, cancer of the esophagus, head and neck cancer, and skin cancer; sialyl Lex-i antigen (SLX), a carbohydrate antigen, which serves as a marker for adenocarcinoma of the lung, cancer of the esophagus, gastric cancer, colon cancer, rectal cancer, pancreatic carcinoma, ovarian cancer, and uterine cancer; SPan-1, a carbohydrate antigen, which serves as a marker for pancreatic carcinoma, biliary tract carcinoma, liver cancer, gastric cancer, and colon cancer; tissue polypeptide antigen (TPA), a single-stranded polypeptide, which serves as a marker for cancer of the esophagus, gastric cancer, colorectal cancer, breast cancer, hepatocellular carcinoma, biliary tract carcinoma, pancreatic carcinoma, lung cancer, and uterine cancer and is particularly useful for the estimation of advanced cancer, precognition of recurrence, and follow-up in combination with other tumor markers; sialyl Tn antigen (STN), a core carbohydrate antigen, which serves as a marker for ovarian cancer, metastatic ovarian cancer, gastric cancer, colon cancer, biliary system cancer, pancreatic carcinoma, and lung cancer; cytokeratin (CYFRA) as a tumor marker effective for the detection of non-small cell carcinoma of the lung, particularly, squamous cell carcinoma of the lung; pepsinogen (PG), an inactive precursor of two pepsins (PG I and PG II) that are proteases secreted into gastric juice, which serves as a marker for gastric ulcer (particularly, gastric ulcer located in the lower part), gastroduodenal ulcer (particularly, recurrent and intractable cases), Brunner's gland adenoma, Zollinger-Ellison syndrome, and acute gastritis; C-reactive protein (CRP), an acute phase reactant changed in serum by tissue injury or infection, which shows high values during myocardial necrosis caused by acute myocardial infarction and the like; serum amyloid A protein (SAA), an acute phase reactant changed in serum by tissue injury or infection; myoglobin, a heme protein with a molecular weight of approximately 17500 present mainly in cardiac muscles and skeletal muscles, which serves as a marker for acute myocardial infraction, muscular dystrophy, polymyositis, and dermatomyositis; creatine kinase (CK; three isozymes of CK-MM type derived from skeletal muscles, CK-BB type derived from brains and smooth muscles, and CK-MB type derived from cardiac muscles, mitochondrial isozyme and immunoglobulin-linked CK (macro CK)), an enzyme present mainly in the soluble fractions of skeletal muscles and cardiac muscles and migrating into blood by cell injury, which serves as a marker for acute myocardial infraction, hypothyroidism, progressive muscular dystrophy, and polymyositis; troponin T, a protein with a molecular weight of 39000 forming a troponin complex with troponin I and troponin C on the thin filaments of striated muscles and participating in the regulation of muscular contraction, which serves as a marker for rhabdomyolysis, myocarditis, myocardial infarction, and renal failure; ventricular myosin light chain I, a protein contained in the cells of both skeletal muscles and cardiac muscles, which serves as a marker for acute myocardial infraction, muscular dystrophy and renal failure because a rise in its measurement result means injury and necrosis in skeletal muscles, and cardiac muscles; and chromogranin A, thioredoxin and 8-OHdG, which have received attention as stress markers in recent years.

Most of the biological substances selected from nucleic acids, proteins, sugar chains, lipids, and complexes thereof are endogenous substances produced by the organisms. In organisms of species different therefrom, such biological substances function as immunogenic substances. Thus, the endogenous substances produced by the organisms can be used as immunogenic substances for the immunization of organisms of species different therefrom to prepare antibodies exhibiting specific reactivity. For example, proteins or complexes containing protein components may be used as immunogens. In this case, plural epitope sites are generally present on the protein molecules having three-dimensional structures. Plural antibodies selectively reacting with these epitope sites, antiserum containing these plural antibodies, or polyclonal antibodies can be prepared.

Alternatively, sugar chains or lipids also often function as immunogens. Antibodies exhibiting specific reactivity thereto can be prepared. Thus, sugar chains or lipids as target substances may be used as immunogens to prepare plural specific antibodies. In such a case, one of the specific antibodies can be used as organic substances in the biological substance-immobilized sensor element according to the present invention. In addition, the organisms themselves may have receptor proteins for their sugar chains or lipids. For the sugar chains or lipids as target substances for which such endogenous receptor proteins are present, these endogenous receptor proteins can be used as organic substances in the biological substance-immobilized sensor element according to the present invention. Particularly, the sugar chains themselves may be constituted to permit the interaction between the sugar chains. In such a case, sugar chain probes using this interaction between the sugar chains can be used in the present invention.

The target substance capturing body has the function of capturing the target substances. Examples of the target substance capturing body can include nucleic acid molecules, peptides or proteins having one or more amino acids, sugar chains, sugar chain-protein complexes, and lipids.

Examples of the nucleic acid molecules include deoxyribonucleic acid molecules and ribonucleic acid molecules. For example, DNA chips use a mechanism in which nucleic acid molecules having nucleotide sequences complementary to the nucleotide sequences of immobilized DNA molecules are recognized through hybridization reaction. Therefore, the DNA molecules are prepared as single-stranded DNA molecules having given nucleotide sequences. In addition, some nucleic acid molecules have been shown to form particular three-dimensional structures and have molecular recognition abilities derived from the three-dimensional structures. Such nucleic acid molecules having molecular recognition abilities derived from the three-dimensional structures are collectively called aptamers. For example, nucleotide sequences having high molecular recognition abilities can be selected and obtained from among diverse nucleotide sequences by molecular evolution engineering approaches typified by SELEX. Furthermore, the nucleotide sequence of double-stranded DNA targeted by DNA-binding proteins has also been identified. Such double-stranded DNA molecules may also be selected as a target substance capturing body applicable to the present invention.

Alternative examples of protein molecules that may be selected as a target substance capturing body include enzymes, antibodies, receptor molecules, and scaffold protein molecules. Examples of the antibody molecules include immune antibody molecules produced as a result of the immune reaction of test animals into which antigen substances have been introduced. Further examples thereof include immunoglobulin molecules collected by a variety of methods, such as recombinant antibody molecules modified in a gene engineering manner from the partial or whole structures of the immune antibodies. These antibodies may be any of monoclonal and polyclonal antibodies. These antibody molecules belong to arbitrary immunoglobulin classes and can be selected from, for example, human IgG, IgM, IgA, IgD, and IgE. Among these classes, particularly, IgG class antibody molecules can be used.

In addition to the immunoglobulin molecules, antibody fragment molecules can also be used. Examples thereof include Fab, Fab', and F(ab')2. For example, Fab fragment molecules are almost the same fragment molecules as antibody fragment molecules obtained by the papain digestion of antibody globulin. F(ab')2 molecules are almost the same fragment molecules as antibody fragment molecules obtained by the pepsin digestion of antibody globulin. These antibody fragment molecules may be prepared by methods which involve enzymatically or chemically decomposing antibody globulin. In most cases, a recombinant production method in a gene engineering manner is also applicable to the preparation. Furthermore, scFv (single chain Fv) can be used. This scFv is a molecule recombinantly produced in a gene engineering manner by linking, via a peptide linker, heavy chain (VH) and light chain (VL) domains constituting variable regions (Fv) as antigen recognition sites in immunoglobulin molecules. The scFv molecules have antigen recognition abilities.

(Method for Producing Target Substance Detection Element)

A method for producing the target substance detection element of the present invention is characterized by including:

(A) preparing a target substance capturing body having a first peptide region specifically recognizing a first layer of plural layers constituting a detection substrate and binding to the first layer and a second peptide region specifically recognizing a second layer different from the first layer of the plural layers and binding to the second layer;

(B) bringing the target substance capturing body into contact with the detection substrate so as to bind the first peptide region of the target substance capturing body to the first layer of the detection substrate and the second peptide region of the target substance capturing body to the second layer of the detection substrate; and (C) removing the target substance capturing body that has specifically recognized only one of the first layer and the second layer and bound to the one of the first layer and the second layer, by utilizing the difference in binding strength between the target substance capturing body that has specifically recognized at least both of the first layer and the second layer and bound to both of the first layer and the second layer and the target substance capturing body that has specifically recognized only one of the first layer and the second layer and bound to the one of the first layer and the second layer.

Thus, the original functions (molecular recognition and catalytic abilities) of the biological substance working as a target substance capturing site can be confirmed beforehand to be exhibited therein in state of linking to the first peptide region and the second peptide region. Moreover, chemical reaction using reagents that reduce the capturing ability of the target substance capturing body is not used for immobilizing the target substance capturing body having the first peptide region and the second peptide region onto the detection substrate. Therefore, the target substance capturing body immobilized on the detection substrate is kept in a state capable of sufficiently exhibiting its functions. In addition, according to a material constituting the first layer, an amino acid sequence having desired binding ability can be selected in advance by screening. According a biological substance working as the target substance capturing site of interest, the binding form of the binding domain bound with the biological substance in advance can be designed. Furthermore, an amino acid sequence having binding ability to a material contained in the binding domain can be designed. Accordingly, both of a base substance material used and the biological substance of interest are applicable in a wide range to the biological substance-immobilized sensor element according to the present invention.

Regarding the Step (A):

The step of preparing a target substance capturing body is achieved by two approaches including:

(A-1) preparing a first peptide region and a second peptide region, and (A-2) binding the first peptide region and the second peptide region to a target substance capturing site; and (A'-1) constructing an expression vector containing first peptide region- and second peptide region-encoding genes inserted upstream or downstream of a target substance capturing site-encoding gene in the same reading frame to stably obtain a target substance capturing body having first and second peptide regions and a target substance capturing site.

Regarding the Step (A-1):

The first peptide region constituting the target substance capturing body can be obtained conveniently, for example, by screening a random peptide library.

Hereinafter, a method for screening a random peptide library for obtaining the first peptide region will be described.

Examples of random peptide libraries that may be used in screening include:

(a) a random synthetic peptide library of random peptides chemically synthesized in a soluble form;

(b) a solid phase-immobilized peptide library synthesized on resin beads;

(c) a peptide library biosynthesized from chemically synthesized DNAs with random sequences in a cell-free ribosome system;

(d) a phage display peptide library prepared by ligating random synthetic genes to N-terminal genes of M13 phage surface proteins (e.g. gene III proteins); and (e) a random peptide library of random peptides displayed by the same approach as in the peptide library (d) as fusions to a bacterial outer membrane protein Omp A (Francisco et al., 1993, Proc. Natl. Acad. Sci. USA, 90, 10444-10448; and Pistor and Hoborn, 1989, Klin. Wochenschr., 66, 110-116), PAL (Fuchs et al., 1991, Bio/Technology, 9, 1369-1372), Lamb (Charbit et al., 1988, Gene, 70, 181-189; and Bradbury et al., 1993, Bio/Technology, 1565-1568), fimbrin (Hedeg Aard and Klem M., 1989, Gene, 85, 115-124; and Hofnung, 1991, Methods Cell Biol., 34, 77-105), and IgA protease β region (Klauser et al., 1990, EMBO J., 9, 1991-1999).

The first peptide region having affinity for the first layer constituting the sensor element is screened using these random peptide libraries. A screening approach using, for example, a chemical synthetic peptide library, is performed as follows: first, the peptide library is adsorbed onto a carrier or substrate (e.g., a column or plate) made of the same material as that constituting the first layer used in the sensor. Then, the peptides having no affinity for the first layer are removed by a washing step. Thereafter, the peptides bound with the first layer are collected to determine the first peptide region. The amino acid sequence of the first peptide region can be determined using Edman degradation or the like.

On the other hand, a phage display peptide library may be used. In such a case, the library is added to the same material as that constituting the first layer. The bound phages are allowed to remain thereon, and the unbound phages are washed away. The phages remaining after washing are eluted with an acid or the like and neutralized with a buffer solution. Then, *E. coli* is infected with the phages to amplify the phages. This selection (panning procedure) is repeated plural times to concentrate plural clones having affinity for the first layer of interest. In this context, for obtaining a single clone, E. coli cells infected again with the phages are seeded onto a medium plate to form colonies. Each single colony is cultured in a liquid medium. Then, the phages present in the supernatant of the medium are precipitated and purified with polyethylene glycol or the like. The nucleotide sequence thereof can be analyzed to determine the amino acid sequence of the first peptide of interest.

The screening of the first peptide region using the phage display peptide library involves so-called a panning procedure. In this panning procedure, phages more strongly binding to the first layer are concentrated. Therefore, this screening approach can select more reliable peptide candidates and can therefore be used suitably for the object of the present invention. The phage display random peptide library may be constructed by a method which involves ligating random synthetic genes to the N-terminal genes of, for example, M13 phage surface proteins (e.g., gene III proteins). Methods thereof have been reported in Scott, J. K. and Smith, G. P., Science Vol. 249, 386 (1990) and Cwirla, S. E. et al., Proc. Natl. Acad. Sci. USA Vol. 87, 6378, (1990). The size of the gene insert is not particularly limited as long as peptides can be expressed stably. The gene insert can have an appropriate length corresponding to 6 to 40 amino acids (which correspond to molecular weight of approximately 600 to 4000), particularly, 7 to 18 amino acids. As a result, the prepared library can cover all random sequences and have affinity.

The first peptide region may be formed by repetitively linking in series the amino acid sequences having affinity to the first layer, which have been obtained by screening the peptide library. Alternatively, two or more types of amino acid sequences may be obtained by screening the peptide library. In such a case, the plural types of amino acid sequences obtained can be selected appropriately and may be combined to form the first peptide region. Moreover, at least one of the plural types of amino acid sequences may contain the full length. In this case, it is desired that an appropriate linker sequence should be provided between the amino acid sequences. The linker sequence can range from approximately 3 to approximately 400 amino acids and may link the amino acids sequences having affinity for the surface material member, without exhibiting adverse effects on the affinity of the first peptide region for the first layer. Moreover, the linker sequence may contain any amino acid that does not inhibit the affinity of the first peptide region for the first layer and the affinity of the second peptide region for the second layer. The linker sequence can be selected within the range of 3 to 15 amino acids in consideration of the expression and stability of the target substance capturing body having first and second peptide regions and a target substance capturing site. Particularly, the most appropriate linker sequence does not hinder the functions of the target substance capturing site and does not hinder the binding of the target substance capturing body to the detection substrate.

The first and second peptide regions can be obtained as amino acid sequences determined by screening the peptide library. In addition, the first and second peptide regions can also be obtained as amino acid sequences determined by rational design according to the chemical properties of the first layer. A library can be constructed with these amino acid sequences. From this library, amino acid sequences having higher affinity can also be selected by the screening method.

The second peptide region can be obtained using the second layer instead of the first layer.

Regarding the Step (A-2):

The first and second peptide regions and the target substance capturing site are bound together by performing the following modification in advance: the target substance capturing site or the binding domain containing the first and second peptide regions, or both, are subjected in advance to chemical modification/conversion without significantly influencing their functions. For example, the introduction of reactive functional groups is used for linking the target substance capturing site and the binding domain. Specifically, examples of the reactive functional groups used for linking the target substance capturing site and the binding domain include combinations of maleimide and sulfanyl (—SH) groups, succinimide and amino groups, isocyanate and amino groups, halogen and a hydroxy group, halogen and a sulfanyl (—SH) group, epoxy and amino groups, and epoxy and sulfanyl (—SH) groups. The target substance capturing site or the binding domain (first and second peptide regions), or both, are subjected to chemical modification/conversion in advance using such combinations. Then, a chemical bond can be formed between the functional groups to form a target substance capturing body.

Furthermore, the target substance capturing site may be a lipid. In such a case, the target substance capturing body structure includes the first peptide region and the second peptide region and additionally includes a "hydrophobic peptide structure" containing plural amino acids with free hydrophobic groups. Examples of the amino acids with free hydrophobic groups include alanine, valine, leucine, isoleucine, methionine, tryptophan, phenylalanine, and proline. In this way, a complex having the target substance capturing site and the first and second peptide regions is formed through the hydrophobic bond to the "hydrophobic peptide structure" of the lipid molecule. This complex can be used as a target substance capturing body.

Regarding the Step (A'-1):

The step (A'-1) may be used instead of the steps (A-1) and (A-2).

This step include constructing an expression vector containing first peptide region- and second peptide region-encoding genes inserted upstream or downstream of a target substance capturing site-encoding gene in the same reading frame. As a result, a target substance capturing body having first and second peptide regions and a target substance capturing site is stably prepared.

A promoter sequence used in the expression vector or an antibiotic resistance gene sequence for transformation confirmation can be selected for use from conventionally known sequences.

The amino acid sequences of the peptides having binding abilities to the materials may be amino acid sequences obtained and determined by the method or may be amino acid sequences rationally designed according to the chemical properties of the material members. Materials known in the art and their affinity peptides known in the art may be applied as surface materials and as binding domains, respectively, to the sensor element according to the present invention. The materials are not particularly limited as described above as long as the materials satisfy the constitution of the sensor element according to the present invention. For example, affinity peptides for inorganic materials (e.g., semiconductors, metals, metal oxide, or insulators containing a protective layer) or affinity peptides for organic materials (e.g., biopolymers such as proteins used as blocking layers in biological reaction, or polymer materials) can be used. Alternatively, materials described in Nature Materials 2003 Vol. 2 577-585 may be used as the base substance surface material according to the present invention. In this case, peptide sequences having binding abilities to various materials disclosed therein may also be used. Alternatively, the peptides having binding abilities to the materials may have the deletion, substitution, or addition of one or several amino acids in their amino acid sequences. Such peptides having modified amino acid sequences may be used without any problem as long as the peptides possess the same affinity for the materials as that of the amino acid sequences before modification. In this context, it is usually desired that the addition of amino acid(s) should be the further addition of an amino acid sequence at the N or C terminus of the amino acid sequence. Moreover, it is usually desired that the deletion of amino acid(s) should be the removal of one or several amino acids in total from the N or C terminus of the amino acid sequence to form a terminally-truncated amino acid sequence. By contrast, it is usually desired that the substitution of amino acid(s) should be amino acid substitution, that is, so-called homologous substitution, for the amino acid(s) to be substituted thereby. Plural variations may be provided unless the total number of amino acids modified exceeds several amino acids. In this case, at least 7 or more, particularly, 8 or more amino acids in the modified amino acid sequence can be the same as those in the original amino acid sequence. Moreover, these amino acid sequences may be repeated wholly or partially in the structures.

Regarding the Step (B):

The step (B) includes preparing an aqueous solution containing the target substance capturing body having the first peptide region and the second peptide region and bringing the solution into contact with the detection substrate having the first layer having affinity for the first peptide region and the second layer having affinity for the second peptide region. As a result, the first peptide region of the target substance capturing body specifically recognizes the first layer and binds to the first layer, and the second peptide region of the target substance capturing body specifically recognizes the second layer and binds to the second layer. Accordingly, the target substance capturing body can be immobilized specifically in the neighborhood of the boundary between the first layer and the second layer.

The target substance capturing body may be brought into contact with the detection substrate by a method which involves dipping the detection substrate in a solution containing the target substance capturing body or by a method which involves adding dropwise the solution to the surface of the detection substrate. For the former method, it is desired that a container in which the detection substrate is brought into contact with the solution containing the target substance capturing body should be shaken or stirred at appropriate strength. Alternatively, for the latter method, it is desired that the detection substrate should be stirred for the contact. In this way, the first peptide region and the second peptide region of the target substance capturing body equally bind to the neighborhood of the boundary between the first layer and the second layer.

A solvent for the mixed solution containing the target substance capturing body may be an aqueous solution. This aqueous solution is allowed to contain the target substance capturing body to prepare the mixed solution. Such an aqueous solution may be any aqueous solution that does not hinder the binding reaction between the immobilized target substance capturing body and a target substance. Specifically, buffer solutions can be used. Examples of the buffer solutions that can be used include general buffer solutions used in biochemical reaction, for example, acetate buffers, phosphate buffers (PBS), potassium phosphate buffers, 3-(N-morpholino)propanesulfonic acid (MOPS) buffers, N-tris(hydroxymethyl)methyl-3-aminopropanesulfonic acid (TAPS) buffers, tris-HCl buffers, glycine buffers, 2-(cyclohexylamino)ethanesulfonic acid (CHES) buffers, and HEPES buffers.

The immobilization treatment alters the surface charge amounts and hydrophobicity of the amino acid sequences contained in the first peptide region and the second peptide region. Therefore, it is desired that the composition of the aqueous solution used should be prepared in consideration of this alternation using the pH or salt concentration of the aqueous medium and a surfactant. The buffer for screening the peptide library can be used. Moreover, the pH and salt concentration can be the same as the conditions for screening the first and second peptide regions.

Regarding the Step (C):

The step (C) utilizes the difference in binding strength between the target substance capturing body that has specifically recognized at least both of the first layer and the second layer and bound to both of the first layer and the second layer and the target substance capturing body that has specifically recognized only one of the first layer and the second layer and bound to the one of the first layer and the second layer. In this step, the target substance capturing body that has specifically recognized only one of the first layer and the second layer and bound to the one of the first layer and the second layer is removed by utilizing this difference.

The former binding strength is stronger than the latter one. In this step, only the latter binding is dissociated using this principle. As a result, the target substance capturing body bound with layers other than the first layer and the second layer, the target substance capturing body bound with layers other than the first layer and with the second layer, and the target substance capturing body bound with layers other than the second layer and with the first layer are removed. Specifically, only the target substance capturing body that is present in the neighborhood of the boundary between the first layer and the second layer and is bound with both of the first layer and the second layer can be immobilized on the substrate.

For performing such a step, the target substance capturing body that has specifically recognized only one of the first layer and the second layer and bound to the one of the first layer and the second layer is removed by washing. Conditions for this washing may be set to conditions under which the target substance capturing body is allowed to remain more selectively in the neighborhood of the boundary between the first layer and the second layer. Specifically, a method for this purpose involves adjusting the composition of a washing solution, a temperature, a washing time, and the number of washes. The composition of a washing solution is selected so that the dissociation constant between the detection substrate and the target substance capturing body bound in both of the first and second peptide regions with the detection substrate can be two or more times, particularly, about an order of magnitude smaller than each dissociation constant between the first or second peptide region and the first or second layer.

Likewise, the composition of an aqueous medium can be selected so that the dissociation constant between the binding domain and the neighborhood region of the boundary is two or more times, particularly, about an order of magnitude smaller than the dissociation constant of specific or non-specific binding between the target substance capturing body and surface materials other than the materials forming the neighborhood region of the boundary. Alternatively, the composition of an aqueous medium can also be selected so that each dissociation constant between the first or second peptide region and the first or second layer is two or more times, particularly, about an order of magnitude smaller than the dissociation constant of specific or non-specific binding between the first or second peptide region and surface materials other than the materials forming the boundary region.

Furthermore, the amount of the first and second peptide regions bound to the boundary between the first layer and the second layer can be measured directly to adjust the composition of the solution. To measure such a bound amount, for example, a target substance capturing body solution with a known concentration is added to the neighborhood region of the boundary between the first layer and the second layer in a certain area to perform immobilization treatment. Then, the concentration of the target substance capturing body remaining in the solution is measured. The bound amount can be determined by subtraction.

An immobilization treatment time for the target substance capturing body can be 1 minute to 48 hours, particularly, 10 minutes to 3 hours. The target substance capturing body left (standing) for an excessive amount of time for immobilization is sometimes reduced in its target substance capturing ability. Therefore, such an approach is not generally preferable.

The target substance capturing body can have a dissociation constant $K_D$ of $10^{-6}$ M or smaller to the detection substrate. As a result, specific binding can be differentiated from non-specific binding. Particularly, the dissociation constant can be $10^{-8}$ M or smaller. The target substance capturing body can have a dissociation constant described below in both of the first peptide region and the second peptide region constituting the binding domain. As a result, non-specific adsorption products can be removed easily by washing in the immobilization of the target substance capturing body. Specifically, the dissociation constants between the first peptide region and the first layer and between the second peptide region and the second layer can be $10^{-6}$ M or smaller.

The desired dissociation constant can be obtained by the sequence selection of the peptide regions, the number of repeats, various sequence variations, and so on. The dissociation constant can be determined by kinetic analysis using a variety of analysis apparatuses. For example, SPR, QCM, or calorimetry apparatuses can be used to determine the dissociation constant.

A detection method according to the present invention includes: bringing a target substance into contact with the target substance detection element including the target substance capturing body and the detection substrate; and obtaining a signal from the target substance detection element so as to detect the presence or absence or amount of the target substance in a sample. Examples of such a signal include changes in refractive index, crystal oscillation frequency, electric potential, magnetism, and labeling substance amount.

An approach for detecting target substances bound onto the base substance of this target substance detection element can be selected appropriately for use from conventionally known detection methods having sensor surface. Examples thereof include SPR, QCM, LSPR, magnetic detection, and electrochemical detection.

For detecting target substances, labeling substances may be used. Examples of such labeling substances include: fine particles of metals (e.g., gold) or organic materials (e.g., latex); fluorescent materials that emit fluorescence by excitation light in a particular wavelength range; and enzymes (e.g., HRP) that produce such fluorescent materials as reaction products. These labeling substances may be used as complexes. Alternatively, these labeling substances can be bound with secondary antibodies to prepare labeling substances. Examples of methods for labeling proteins such as secondary antibodies include: a method using physical adsorption; and a chemical bond method which involves introducing reactive functional groups into labeling substances or substances to be labeled and forming a chemical bond with the functional groups as cross-linking points. To bind labeling substances and secondary antibodies to target substances, the target substances are bound with the labeling substances in advance to form complexes of the target substances and the labeling substances, which may then be detected by capturing the complexes by the target substance capturing body present on the detection substrate surface. Alternatively, the target substances may be captured by the target substance capturing body present on the detection substrate surface and then further labeled with the labeling substances for detection.

Monoclonal antibodies can be used as such labeling substances. The labeling site in the target substances labeled with the labeling substances is different from an epitope site against the monoclonal antibodies. Alternatively, an antibody group (polyclonal antibody) containing such monoclonal antibodies can be used. In some cases, the binding of the target substance capturing body to target substances may cause the expression of an epitope absent in the target substances themselves. In this case, antibodies specifically reactive with the epitope site specific to the complexes of the labeling substances and the target substances can be used as more highly selective secondary antibodies.

Conventionally known detection methods can be used as methods for detecting a label provided on the substance specifically recognizing and binding to target substances. Conventionally known labeling substances, for example, fluorescent materials, luminescent materials, metals, and metal oxide fine particles, may be used as labeling substances provided on the secondary antibodies. These labeling substances may improve detection sensitivity.

Examples of the fluorescent materials that may be used in labeling include conventionally known fluorescent dyes such as 4-methylumbelliferone, 7-hydroxy-4-biphenyl-umbelliferone, 3-hydroxy-2-naphthoic 2-phenylanilide, 3-hydroxy-2-naphthoic 2,4-dimethylanilide, 6-bromo-2-hydroxy-3-naphthoic 2-methylanilide, 3-hydroxy-2-anthranoic 2-methylanilide, pyrene, fluorescein, perylene, rhodamine, and Texas red.

Examples of the luminescent materials that may be used in labeling include luminol, luminol derivatives, luciferin, and lucigenin widely used.

Examples of the metals that may be used in labeling include metallic element-containing fine particles conventionally used that contain arbitrary metallic elements such as gold, silver, copper, platinum, zinc, aluminum, alkali metal elements (e.g., lithium and potassium), alkali earth metal elements (e.g., beryllium, magnesium, and calcium), and metals that are magnetized (e.g., iron, cobalt, and nickel). For example, a plasmon resonance method is used suitably for the detection of labeling with these fine particles because of its high sensitivity. Thus, examples of the metals that can be used include, but not limited to, metal elements such as gold, silver, copper, aluminum, zinc, and potassium that easily cause plasmon resonance.

Examples of semiconductor fine particles that may be used in labeling include semiconductor nanoparticles such as ZnS, ZnSe, ZnTe, CdS, CdSe, CdTe, InGaAs, and InP. Alternatively, such semiconductor fine particles encompass not only fine particles formed of one semiconductor type but also semiconductor fine particles covered with a semiconductor material having a wider band gap. It is desired that these semiconductor fine particles should have a particle size selected in the range of 1 nm to 50 nm, particularly, 2 to 20 nm.

Examples of fine particles of ferromagnetic materials that may be used in labeling can include $Fe_3O_4$, $\gamma$-$Fe_2O_3$, Co-$\gamma$-$Fe_2O_3$, $(NiCuZn)O.Fe_2O_3$, $(CuZn)O.Fe_2O_3$, $(Mn.Zn)O.Fe_2O_3$, $(NiZn)O.Fe_2O_3$, $SrO.6Fe_2O_3$, $BaO.6Fe_2O_3$, and $Fe_3O_4$ covered with $SiO_2$, (particle size: approximately 20 nm) [see Enzyme Microb. Technol., vol. 2, p. 2-10 (1980)]. Further examples thereof can include conjugated fine particles of a variety of polymer materials (nylon, polyacrylamide proteins, etc.) and ferrites.

In the target substance detection element of the present invention, the target substance capturing body can be immobilized only in a particular region. Therefore, the target substance detection element can have parts with high detection sensitivity and parts with low detection sensitivity. Examples of sensors to which the target substance detection element of the present invention is applicable include: SPR sensors that have electric field strength distribution in the z-axis direction relative to the sensor surface and detects changes in dielectric constant; and LSPR sensors that have electric field strength distribution in a three-dimensional pattern relative to the sensor surface. Alternatively, examples of magnetic sensors include TMR or Hall sensors that have magnetic field strength distribution in a three-dimensional pattern relative to the sensor surface. The application of the target substance detection element to magnetic sensors requires labeling, with magnetic molecule, target substances or molecules, such as secondary antibodies, specifically binding to target substances. The labeling substances described above can also be applied to the sensors using an electromagnetic field in target substance detection.

Moreover, the detection apparatus according to the present invention is appropriate to applications for detecting a target substance in a sample. The detection method according to the present invention is exclusively applied to the detection schemes of the detection apparatus. Thus, the exemplary aspects of the detection method according to the present invention can also be used in the detection apparatus according to the present invention.

EXAMPLES

Hereinafter, the present invention will be described more specifically with reference to Examples. However, the scope of the present invention is not limited to Examples below.

Soluble hen egg-white lysozyme proteins (HEL; Seikagaku Corp. code No. 100940) are used as target substances. Moreover, anti-HEL polyclonal antibodies (Anti-HEL; ROCKLAND Inc. code No. 200-4672 (Anti-Lysozyme, Hen Egg White, Rabbit-Poly, Biotin)) and streptavidin-coated magnetic fine particles (SA-Beads; Invitrogen Corporation code No. DB65001 (Dynabeads MyOne Streptavidin 1 μm)) are used in combination as labeling substances.

Recombinant DNA methods described below are performed based on Sambrook et al., Molecular Cloning: A Laboratory Manual, Vol. 2, Cold Spring Harbor Laboratory, New York (1989). Examples of biosensors are disclosed which use the present sensor element as LSPR and Hall elements. Each element can be produced by a method using conventionally known deposition, photolithography, and etching techniques.

Example 1

Production of Target Substance Detection Element Having First Peptide Region and Second Peptide Region HEL-binding scFv (HyHEL10) as a target substance capturing site, a gold (Au)-binding peptide region as a first peptide region, and a silicon oxide ($SiO_2$)-binding peptide region as a second peptide region are used to prepare a fusion protein. Specifically, an Au-binding peptide region (MHGKTQATSGTIQS)×3(SEQ ID NO 5) is linked via a linker sequence (GGGGS)×3 (SEQ ID NO 7) to the C-terminus of HEL-binding scFv (Biophysical Journal Vol. 83, 2946-2968 (2002)) and further linked to an $SiO_2$-binding peptide region (IPMHVHHKHPHV)×2 (SEQ ID NO 6) via a linker sequence (SASGSGGGGSGGGSGGGSEGGG-SEGGGSGGGSGS: SEQ ID NO 8) between the first peptide region and the second peptide region to prepare a fusion. Hereinafter, these steps will be described.

(1) Expression Vector Preparation

The DNA sequence of HEL-binding scFv (HyHEL10) is known in the art. The Au— and $SiO_2$-binding peptide region sequences and each linker sequence that can be used are shown in FIGS. 7A to 7D. Accordingly, for example, synthetic oligonucleotides are can be designed to obtain a target substance capturing body-encoding DNA sequence by overlapping PCR (Sambrook et al., 1989, ibid.). The arrangement of functional regions is illustrated in FIG. 4. This fusion sequence (SEQ ID NO: 1) is illustrated in FIGS. 5 and 6. FIG. 4 illustrates sc-Fv-HyHEL10 24, a (G4S)3 linker 25, a linker 26 between material-binding peptides, an Au-binding peptide region 27, and an $SiO_2$-binding peptide region 28. The DNA sequence encoding the fusion is subjected at the final step to PCR using primers 1 and 2 (SEQ ID NOs: 2 and 3; Table 1) for introducing a restriction enzyme NcoI site into the 5' terminus and a restriction enzyme EagI site into the 3' terminus. The PCR reaction is performed with a commercially available PCR kit (Takara Bio LA-Taq kit) according to the protocol recommended by the manufacturer.

TABLE 1

PCR primer sequence

| Sequence | Restriction enzyme | SEQ ID No. |
|---|---|---|
| Primer 1 NNNNNNNATAGCA<u>CCATGG</u>CCGATATCGTCCTGACCCAGA | NcoI | 2 |
| Primer 2 NNNNNNNTGCTAT<u>CGGCCG</u>CGCCACGTGCGGGTGTTTATGG | EagI | 3 |

*The recognition sequences of restriction enzymes are boxed. Complementary sequences of the fusion DNA are underlined. N denotes any base.

After PCR reaction, the obtained PCR product is subjected to 2% agarose electrophoresis to collect a DNA fragment with the base length of interest as a band. Next, crude extraction from the gel is performed with a gel extraction kit (Promega Inc.) to obtain a DNA fragment of approximately 1000 bp.

Then, the DNA fragment is cleaved with NcoI and EagI restriction enzymes. A pET-20b (+) vector (Novagen Inc.) having *E. coli* secretion signal pelB is used as a recipient vector and cleaved with NcoI/EagI. Then, the fusion DNA fragment containing NcoI/EagI introduced at the termini is ligated to the NcoI/EagI site of the pET-20b (+) vector (Novagen Inc.) using a commercially available T4 ligase kit (Roche Inc.) prepared by a method recommended by the manufacturer.

Next, the ligation reaction solution is used to transform 40 μL of JM109 competent cell solution. The transformation is performed under heat shock conditions involving: in ice→42° C.×90 sec.→in ice. 750 μL of LB medium is added to the JM109 solution transformed by heat shock. The cells are shake-cultured at 37° C. for 1 hour. After centrifugation at 6000 rpm for 5 minutes, 650 μL of the culture supernatant is discarded. The remaining culture supernatant and precipitated cell fractions are stirred. The mixture is spread over an LB/amp. plate and left standing overnight at 37° C. Colonies are randomly selected from the plate. Each colony is shake-cultured in 3 mL of LB/amp. liquid medium. The bacterial cells are collected from the culture solution. Then, a plasmid is extracted from the recombinant bacterial strain with a commercially available MiniPrep Kit (manufactured by Promega Inc.) according to a method recommended by the manufacturer. The collected plasmid is finally sequenced to confirm that the plasmid has the nucleotide sequence of interest in a correct frame.

The sequenced plasmid is used to transform competent cells in 40 μL of BL21 (DE3) solution. The transformation is performed by the same heat shock method as above. 750 μL of LB medium is added to the BL21 solution containing the strains transformed by heat shock. The cells are shake-cultured at 37° C. for 1 hour. After centrifugation at 6000 rpm for 5 minutes, 650 μL of culture supernatant is discarded. The remaining culture supernatant and precipitated cell fractions are stirred. The mixture is spread over an LB/amp. plate and left standing overnight at 37° C.

(2) Preliminary Culture

Colonies on the plate are randomly selected and shake-cultured overnight at 28° C. in 3.0 mL of LB/amp. medium.

(3) Main Culture

The preliminary culture solution is inoculated into 1 L of TB+0.5% glucose medium and further cultured at 28° C. At a point in time when the OD600 of the culture solution exceeds 0.8, IPTG is added thereto at a final concentration of 1 mM. The cells are further cultured overnight at 28° C.

(4) Purification

A fusion expressed in the transformant is secreted into the culture supernatant. This fusion is isolated and purified according to the following steps:

(i) Concentration of Culture Supernatant 10 ml of protease inhibitor cocktail (EDTA-free, 100×) (Nacalai Tesque, Inc. code: 03969-21) is added to 1 L of the bacterial cell culture solution obtained by the main culture. Subsequently, the solution is concentrated to approximately 20 ml with a crossflow filtration (Vivaflow 200 flipflow filtration, MWCO: 10000, PES model VF20P0) apparatus.

(ii) Dialysis

Next, to remove low-molecular-weight compounds and so on in the concentrated medium, the solution is dialyzed at 4° C. against a Tris buffer (pH 8.0) as an external solution.

(iii) Metal Chelate Column Purification of Polypeptide Having His tag

A metal chelate column carrier His-Bind (manufactured by Novagen Inc.) is used in column purification using a His tag. Column preparation, sample loading, and column washing steps are performed at 4° C. under conditions according to a method recommended by the manufacturer. After sample loading and column washing steps, the His tag-fused polypeptide adsorbed on the metal chelate column is eluted with 100 mM imidazole/Tris solution. The eluate is analyzed by electrophoresis on SDS-PAGE (acrylamide 15%) to confirm that a single band is observed. The apparent molecular weight of the substantially single band observed corresponds to the polypeptide chain of interest. Thus, the polypeptide is confirmed to be purified.

(iv) Gel Filtration Purification

The column-eluted sample is loaded in an AKTA 10 s apparatus (GE Healthcare) equipped with a gel filtration column (Superdex 200 pg 10/300 GL). Next, gel filtration is performed with a Tris buffer (pH 8.0) at a flow rate of 0.5 ml/min. to obtain a fraction having the size of interest. The fraction is analyzed by SDS-PAGE (acrylamide 15%) and western analysis (HRP-labeled anti-His antibodies) to confirm that the protein of interest is obtained as a single fraction.

(v) Dialysis

The collected protein solution is further dialyzed against an external solution changed to a phosphate buffer (hereinafter, referred to as PBS, pH 7.4) to convert the buffer solution. The PBS (pH 7.4) solution of the fusion protein is obtained.

Example 2

Immobilization of Target Substance Capturing Body onto First Layer and Second Layer (i) Production of Detection Substrate Having First Layer and Second Layer First, a slide glass is ultrasonically washed in an acetone solution for 30 minutes to remove organic substances. Subsequently, the slide glass is ultrasonically washed in IPA, EtOH, and ultrapure water in this order. The slide glass is stored in new ultrapure water until a subsequent step. Moisture on the slide glass is removed with $N_2$ gas. Half the surface of the slide glass is covered with aluminum foil for leaving the glass surface uncoated, and the slide glass is loaded in a vacuum deposition apparatus. Chromium and gold films in this order are formed on the slide glass by electron beam irradiation. The chromium and gold layers are 2 nm and 200 nm, respectively, in thickness. The aluminum foil-coated region in the prepared structure can be used as a first layer, and the formed gold layer can be used as a second layer. Finally, the prepared structure is dipped in concentrated hydrochloric acid (O/N) and subsequently sonicated in a solution changed to acetone, IPA, EtOH, and ultrapure water to completely wash the gold and glass surfaces. The structure is stored in ultrapure water until target substance capturing body immobilization.

(ii) Binding of Target Substance Capturing Body to Detection Substrate and Study on Washing Conditions The target substance capturing body solution (PBS, pH 7.4) obtained in Example 1 is adjusted to a final concentration of 1 μM. In this adjustment, a surfactant Tween 20 is added thereto at a final concentration of 0.1% (PBST buffer). Moisture on the structure thus prepared is removed with $N_2$ gas. 100 μl of each protein solution is spotted onto the boundary region between the materials. The structure is covered with a cover glass and left at room temperature for 30 minutes in a moisture chamber to prevent drying.

After light washing with PBST, the structure is treated in the same way with 0.5% bovine serum albumin (BSA, PBST buffer) for the purpose of preventing non-specific binding. Then, the treated slide glass is dipped in 1 L each of a variety of buffers shown below and washed for 5 minutes by stirring with a stirrer. This washing is performed 3 times with the buffer changed to new one. Washing temperatures are room temperatures of 25° C. and 37° C.

A surfactant Tween 20 concentration in the composition of a buffer is selected from 0%, 0.001%, 0.01%, 0.1%, 0.5%, and 1%. Moreover, a sodium chloride concentration in a PBS buffer is selected from 1 mM, 20 mM, 50 mM, 100 mM, 200 mM, 500 mM, and 1 M. Buffers are prepared by combining these concentration conditions. In this context, the buffer solution is indicated by the initials of the components and their concentrations. For example, a PBST buffer having a Tween 20 concentration of 0.01% and a sodium chloride concentration of 20 mM is referred to as PBS-T0.01/N20.

(iii) Validation of Selective Arrangement

200 μl of 500 nM HEL proteins is added dropwise as target substances to the neighborhood of the boundary region between the gold layer and the glass layer of the slide glass completely washed in the step (ii). The slide glass is covered with a cover glass. After reaction at room temperature for 30 minutes, the slide glass is washed with each buffer. Next, 1 ml of 100 nM FITC-labeled HEL polyclonal antibodies was spotted thereonto and incubated in a moisture chamber. Then, the slide glass is washed with each buffer. FITC fluorescence at 520 nm is observed with a fluorescence microscope.

As a result, the FITC fluorescence can be observed to be selectively immobilized in the neighborhood of the boundary between the gold layer and the glass layer. In other words, this shows that the immobilized target substance capturing bodies are selectively arranged in the neighborhood of the boundary between the gold layer and the glass layer. The FITC-labeled anti-HEL antibodies having binding abilities to HEL captured by the target substance capturing bodies are specifically bound with HEL. Thus, the FITC as a labeling substance can be confirmed selectively in the neighborhood of the boundary region between the gold layer and the glass layer, in a reflection of the selective arrangement of the target substance capturing bodies. At both of the washing temperatures of 25° C. and 37° C., it is observed that with increases in salt concentration, FITC fluorescence remains in slightly lager amounts in both of the gold and glass surfaces other than the neighborhood of the boundary between the gold layer and the glass layer. This demonstrates increased binding other than that of both the gold- and glass-binding peptides of the target substance capturing bodies. With increases in the amount of the surfactant, FITC fluorescence from the gold glass surface including the boundary between the gold layer and the glass layer is reduced as a whole. This can demonstrate reduced binding to the neighborhood of the boundary between the first layer and the second layer via both the gold- and glass-binding peptides of the target substance capturing bodies. Among buffer combinations, PBS-T0.001, -T0.01, or —T0.1/N20, N50, N100, N200, or N500 (NaCl concentration) can be expected to produce selective immobilization, substantial binding, and target substance-binding abilities. In Examples below, the PBS-T0.1-N100 buffer is used in washing (37° C.) and target substance binding (room temperature).

Example 3

Demonstration of LSPR Detection (i) LSPR Element Production and Detection Apparatus (FIG. 10)

FIG. 8 illustrates the outlined structure of a detection apparatus used in this Example. A gold thin film of 20 nm in film thickness is formed on a quartz substrate 22 of 625 μm in thickness. This gold thin film can be patterned into a given metal structure pattern with an electron beam writer to produce an element 18. The planar outer shape of the metal structure in the element 18 produced in this Example is a 200 nm×200 nm square. The chromium layer of 2 nm is provided as a base for the gold thin film. The patterns are arranged in an array form in a 3 mm×3 mm region at spacing of 250 nm (see FIG. 10). Such patterns have been known to have electric field strength distribution in the surroundings of the metal structure and have high electric field strength in the substantially rectangular prism-shaped edge region of the metal structure, particularly, in the vicinity of the vertex on the reaction region side and in its surroundings.

(ii) Immobilization of Target Substance Capturing Body

To impart capturing ability to the metal structure surface of the LSPR element, the target substance capturing bodies obtained in Example 1 are added at a concentration of 1 μM to the PBS-T0.1-N100 buffer to prepare a solution. This solution is allowed to act on the element and incubated at room temperature for 30 minutes in a moisture chamber. Next, the washing step of Example 2 is performed at 37° C. with the PBS-T0.1-N100 buffer to remove fusion proteins bound with regions other than the neighborhood of the boundary between the gold layer and the glass layer.

For a reference experiment, an LSPR element is dipped in 1 mM amino-undecathiol by stirring for 2 hours. After washing with ultrapure water, the amino group on the gold surface is activated with EDC/NHS (EDC: 1-ethyl-3-(3-dimethylaminopropyl)-carbodiimide; NHS: N-hydroxysuccinimide). Then, target substance capturing bodies are allowed to act thereon and incubated for 30 minutes in a moisture chamber. After washing with ultrapure water, the activated amino group is blocked with ethanolamine. In this way, a control sensor element can be prepared in which the target substance capturing bodies are randomly immobilized. Finally, 0.5% BSA solution (PBS-T0.1-N100 buffer) is allowed to act on both of the elements for preventing non-specific adsorption, and the elements are washed. The elements thus prepared are: an LSPR element in which the target substance capturing bodies having the gold- and glass-binding peptides are immobilized in the neighborhood of the boundary between the gold layer and the glass layer; and a control LSPR element in which the target substance capturing bodies are immobilized randomly and almost homogeneously on the sensor surface.

A target substance HEL concentration in a sample can be measured specifically with the detection apparatus illustrated in FIG. 8 by the following procedures:

(1) a sample containing HEL as target substances is introduced through an inlet 19 into the produced element 18. The HEL is captured on the structure. In this context, FIG. 8 illustrates an outlet 20 and a substrate 22;

(2) the sample is discharged therefrom, and the PBS-T0.1-N100 buffer is introduced through the inlet 19 thereinto to wash the inside of a reaction well 21;

(3) biotinylated anti-HEL polyclonal antibodies as labeling substances adjusted to a final concentration of 100 nM with the PBS-T0.1-N100 buffer are reacted with the HEL immobilized on both the elements;

(4) the labeling substances are discharged therefrom, and the PBS-T0.1-N100 buffer is introduced through the inlet 19 thereinto to wash the inside of the reaction well 21; and (5) finally, the PBS-T0.1-N100 buffer is charged thereinto, and the absorption spectrum of the gold structure is measured. In this context, FIG. 8 illustrates a tungsten lamp 16, a collimator lens 17, and a spectrophotometer 23.

The absorption spectrum is compared between before and after reaction. FIG. 9 illustrates one example thereof. As seen in FIG. 9, the target substances and further, the labeling substances bind to the detection element surface through specific antigen-antibody reaction so as to shift the absorption spectrum. In this context, the correlation between the amount of shift of absorption spectrum peak strength or peak wavelength and a HEL concentration is determined in advance with a known HEL control solution. As a result, the concentration of a very small amount of HEL in the sample with an unknown concentration can be determined.

The use of such a target substance detection element can be expected to obtain the excellent concentration to the amount of shift of peak strength or peak wavelength detectable depending on a target substance concentration. In other words, the randomly immobilized target substance capturing bodies as reference are almost homogeneously immobilized on the element surface having electric field strength distribution. Target substances are reacted stochastically with these immobilized target substance capturing bodies. As a result, binding occurs regardless of electric field strength. Therefore, variation in refractive index (dielectric constant) response derived from the bound target substances may result. Furthermore, in a lower concentration region of target substances, detection signals are dominated by the bound parts on the element surface. In such a case, the total concentration value as a detection limit might be higher. On the other hand, in the target substance detection element of this Example, the boundary between the gold layer and the glass layer is selected so that the target substance capturing bodies can be immobilized in a region with strong electric field strength (in this Example, the edge region having a nano pattern structure formed with the gold material). Therefore, refractive index response derived from target substances is improved and rendered more homogeneously. As a result, the target substances even with a low concentration can be detected with good correlation. Specifically, the target substance detection element of this Example achieves improvement in the orientation of the immobilized target substance capturing bodies and the effective immobilization thereof in a region with strong electric field strength. Thus, the target substance detection element can be expected to have the effect of improving a detection limit as compared with conventional one.

Example 4

Demonstration of Magnetic Detection (i) Hall Sensor Element Production and Detection Apparatus FIG. 10 illustrates the structure of a Hall sensor used in this Example and a detection circuit. The Hall sensor used in this Example has a p-HEMT structure generally used in magnetic field measurement with high sensitivity. The present invention is not limited to this structure or material. Hall sensors having any structure or material are applicable to the present invention. A Hall sensor 29 having a p-HEMT structure is produced as follows: a superlattice film including GaAs and AlGaAs thin films, that is, a GaAs film of 800 nm, an InGaAs film of 12 nm, an AlGaAs film of 40 nm, and an n-GaAs film of 20 nm are formed in this order on a GaAs substrate 30 by a CVD coating method. The prepared multilayered film is processed into a cross element by a semiconductor process generally used. An etching depth is approximately 80 nm. The element is 20 μm in width and has a central portion of 20 μm×20 μm square. This square region serves as a magnetic field detection region. Moreover, the element is surrounded by an $SiO_2$ insulating film (interlayer insulating film) of 80 nm. Then, an AuGe film of 50 nm is deposited thereonto to form electrodes (31) at four ends of the element. Two of these four electrodes are used for producing detection currents. The other two electrodes are used for obtaining Hall voltages (detection signals). The Hall element is coated by a CVD coating method with an $SiO_2$ film of 50 nm. An Au film of 20 nm in film thickness is further formed by a sputtering coating method in the vicinity of the interface between the magnetic field detection region of the Hall element and the electrodes for obtaining Hall voltages. Then, the Hall element is coated again with an $SiO_2$ film of 50 nm. The $SiO_2$ film 33 and the Au film 34 on the magnetic field detection region 32 of the Hall element are removed by a dry etching method to expose the cross-section of the Au film in the partial neighborhood of the magnetic field detection region.

The Hall sensor obtained by the production process is connected with a power supply 35 for producing detection currents and a lock-in amplifier 36 for obtaining detection signals. To magnetize magnetic fine particles, a DC magnetic field (bias magnetic field) is applied in the direction perpendicular to the film surface of the Hall sensor using a coil (37: coil for bias magnetic field application). This DC magnetic field has a size that saturates the magnetization of the magnetic fine particles. In this case, a DC power supply 38 is used. The magnetic fine particles are detected by detecting a stray magnetic field generated from the magnetic fine particles using the Hall sensor. For sensitive detection, the magnetization of the magnetic fine particles is oscillated in the horizontal direction. Changes in stray magnetic field caused thereby are read. To oscillate the magnetization of the magnetic fine particles in the horizontal direction, an AC magnetic field (probe magnetic field) is applied in the in-plane direction of the film surface of the Hall sensor using a coil (39: coil for probe magnetic field application). In this case, an AC power supply 40 is used. When the frequency of the probe magnetic field is defined as f, changes in stray magnetic field generated from the magnetic fine particles have a frequency of 2 f. Thus, only signals having a frequency of 2 f may be detected with the lock-in amplifier so as to detect the magnetic fine particles with high sensitivity. The size of the stray magnetic field differs depending on the number of the magnetic fine particles immobilized on the Hall sensor element surface. Therefore, the number of the magnetic fine particles can be determined from the obtained signal strength.

(ii) Labeling of Target Substance with Magnetic Substance

The target substance capturing bodies obtained in Example 1 is added at a concentration of 1 μM to the PBS-T0.1-N100 buffer to prepare a solution. This solution is added dropwise onto the Hall sensor element illustrated in FIG. 10 and incubated at room temperature for 30 minutes in a moisture chamber. Next, the washing step of Example 2 is performed at 37° C. with the PBS-T0.1-N100 buffer to remove fusion proteins bound with regions other than the boundary region between the materials. For a reference experiment, a HALL sensor element is dipped in 1 mM amino-undecathiol by stirring for 2 hours. After washing with ultrapure water, the amino group on the gold surface is activated with EDC/NHS. Then, target substance capturing bodies are allowed to act thereon for 30 minutes and immobilized on the element. After washing with ultrapure water, the unbound activated amino group is blocked with ethanolamine. In this way, a control sensor element can be prepared in which the target substance capturing bodies are randomly immobilized. Finally, 0.5% BSA solution (PBS-T0.1-N100 buffer) is reacted with both of the elements for preventing non-specific adsorption, and the elements are washed. Next, HEL proteins as target substances are added dropwise onto the sensor surfaces. The elements are covered with a cover glass. After reaction at room temperature for 30 minutes, the elements are washed with a buffer.

A target substance HEL concentration in a sample can be measured specifically by the following procedures:
(1) a sample containing HEL as target substances is allowed to act on the produced elements. The HEL is captured on the structures;
(2) the elements are washed with the PBS-T0.1-N100 buffer to remove the unreacted sample;
(3) biotinylated anti-HEL polyclonal antibodies as labeling substances adjusted to a final concentration of 100 nM with the PBS-T0.1-N100 buffer are reacted with the HEL immobilized on both of the elements;
(4) the elements are washed with the PBS-T0.1-N100 buffer to remove the unreacted labeling substances;
(5) subsequently, streptavidin-coated magnetic fine particles (SA-Beads; Invitrogen Corporation code No. DB65001 (Dynabeads MyOne Streptavidin 1 μm)) are allowed to act on the biotin as a label on the immobilized HEL. The magnetic fine particles specifically bind thereto through biotin-avidin reaction caused by this action; and
(6) finally, the elements are washed with the PBS-T0.1-N100 buffer. Then, the magnetic sensor surfaces are dried with $N_2$ gas. Magnetic detection is performed.

In this context, the correlation between the amount of shift of the magnetic field of the magnetic sensor element attributed to a stray magnetic field derived from the magnetic fine particles and a HEL concentration is determined in advance with a known HEL control solution. As a result, the concentration of a very small amount of HEL in the sample with an unknown concentration can be determined. In another method, the number of biotin per antibody as a labeling substance and the number of the magnetic fine particles per streptavidin are controlled to some extent. In this case, the number of the magnetic fine particles can be estimated from the amount of shift of magnetic field strength. Thus, the quantitative analysis of a target substance concentration can be achieved directly.

(iii) Magnetic Detection

The use of the target substance detection element of this Example can be expected to exhibit the good correlation with magnetic strength detectable depending on a target substance concentration. In the Hall sensor, a local magnetic field may be applied to a region smaller than the magnetic field detection region. In such a case, signal strength differs depending on the position of the magnetic field applied. Specifically, in conventional techniques, magnetic fine particles are randomly immobilized in a magnetic field detection region. In this case, signal strength differs depending on the position of the magnetic fine particles immobilized. Thus, the number of the magnetic fine particles cannot be detected with good precision. On the other hand, in the sensor element according to the present invention, the magnetic fine particles can be immobilized at a position that gives a constant ratio between the size of the applied magnetic field and the size of the detection signal. Thus, the number of the magnetic fine particles can be detected with good precision. Furthermore, the target substance detection element of this Example achieves improvement in the orientation of the immobilized target substance capturing bodies and the effective immobilization thereof in a region with strong magnetic field strength. Thus, the target substance detection element can be expected to have the effect of improving a detection limit as compared with conventional one.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-074857, filed Mar. 22, 2007, which is hereby incorporated by reference herein in its entirety.

The invention claimed is:

1. A target substance detection element for detecting the presence or absence or concentration of a target substance in a sample, wherein:
   the target substance detection element comprises at least a detection substrate and a target substance capturing body immobilized on the surface of the detection substrate;
   the detection substrate has a first layer including a portion of the surface of the detection substrate and a second layer including a portion of the surface of the detection substrate and being different from the first layer;
   the first layer and the second layer are made of different materials;
   the target substance capturing body has at least a first peptide region specifically recognizing the first layer and binding to the first layer, a second peptide region specifically recognizing the second layer and binding to the second layer, and a target substance capturing site; and
   the first layer and the second layer are adjacent to each other.

2. The target substance detection element according to claim 1, wherein the target substance capturing body has a linker having one or more amino acid(s) between the first peptide region and the second peptide region.

3. The target substance detection element according to claim 1, wherein the first peptide region and the second peptide region have different amino acid sequences.

4. The target substance detection element according to claim 1, wherein the first layer is a detection part.

5. A method for producing a target substance detection element, comprising:

preparing a detection substrate having, on the surface, at least a portion of a first layer and of a second layer made of a material different from that of the first layer;

preparing a target substance capturing body having a first peptide region specifically recognizing the first layer and binding to the first layer, a second peptide region specifically recognizing the second layer and binding to the second layer, and a target substance capturing site, the second layer being different from the first layer and being made of a material different from that of the first layer;

bringing the target substance capturing body into contact with the detection substrate so as to bind the first peptide region of the target substance capturing body to the first layer and the second peptide region of the target substance capturing body to the second layer of the detection substrate; and removing the target substance capturing body that has specifically recognized only one of the first layer and the second layer and bound to the one of the first layer and the second layer, by utilizing the difference in binding strength between the target substance capturing body that has specifically recognized at least both of the first layer and the second layer and bound to both of the first layer and the second layer and the target substance capturing body that has specifically recognized only one of the first layer and the second layer and bound to the one of the first layer and the second layer.

* * * * *

SEQUENCE LISTING

```
<160> NUMBER OF SEQ ID NOS: 8

<210> SEQ ID NO 1
<211> LENGTH: 354
<212> TYPE: PRT
<213> ORGANISM: Artificial
<220> FEATURE:
<223> OTHER INFORMATION: Chimeric protein
<220> FEATURE:
<221> NAME/KEY: ScFv-VL peptide
<222> LOCATION: (1)..(108)
<220> FEATURE:
<221> NAME/KEY: linker peptide
<222> LOCATION: (109)..(123)
<220> FEATURE:
<221> NAME/KEY: ScFv-VH peptide
<222> LOCATION: (124)..(237)
<220> FEATURE:
<221> NAME/KEY: linker peptide
<222> LOCATION: (238)..(252)
<220> FEATURE:
<221> NAME/KEY: Au-binding peptide
<222> LOCATION: (253)..(296)
<220> FEATURE:
<221> NAME/KEY: linker peptide
<222> LOCATION: (297)..(330)
<220> FEATURE:
<221> NAME/KEY: SiO2-binding region
<222> LOCATION: (331)..(354)
```

-continued

<400> SEQUENCE: 1

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Thr Ala Gly Gly Gly Gly
            100                 105                 110

Ser Gly Gly Gly Gly Ser Gly Gly Gly Ser Asp Ile Gln Leu Gln
        115                 120                 125

Glu Ser Gly Pro Ser Leu Val Lys Pro Ser Gln Thr Leu Ser Leu Thr
130                 135                 140

Cys Ser Val Thr Gly Asp Ser Ile Thr Ser Asp Tyr Trp Ser Trp Ile
145                 150                 155                 160

Arg Lys Phe Pro Gly Asn Arg Leu Glu Tyr Met Gly Tyr Val Ser Tyr
                165                 170                 175

Ser Gly Ser Thr Tyr Tyr Asn Pro Ser Leu Lys Ser Arg Ile Ser Ile
            180                 185                 190

Thr Arg Asp Thr Ser Lys Asn Gln Tyr Tyr Leu Asp Leu Asn Ser Val
        195                 200                 205

Thr Thr Glu Asp Thr Ala Thr Tyr Tyr Cys Ala Asn Trp Asp Gly Asp
    210                 215                 220

Tyr Trp Gly Gln Gly Thr Leu Val Thr Val Ser Ala Ala Gly Gly Gly
225                 230                 235                 240

Gly Ser Gly Gly Gly Gly Ser Gly Gly Gly Ser Met His Gly Lys
                245                 250                 255

Thr Gln Ala Thr Ser Gly Thr Ile Gln Ser Met His Gly Lys Thr Gln
            260                 265                 270

Ala Thr Ser Gly Thr Ile Gln Ser Met His Gly Lys Thr Gln Ala Thr
        275                 280                 285

Ser Gly Thr Ile Gln Ser Met His Ser Ala Ser Gly Ser Gly Gly Gly
    290                 295                 300

Gly Ser Gly Gly Gly Ser Gly Gly Gly Glu Gly Gly Gly Ser Glu
305                 310                 315                 320

Gly Gly Gly Ser Gly Gly Gly Ser Gly Ser Ile Pro Met His Val His
                325                 330                 335

His Lys His Pro His Val Ile Pro Met His Val His His Lys His Pro
            340                 345                 350

His Val

<210> SEQ ID NO 2
<211> LENGTH: 39
<212> TYPE: DNA
<213> ORGANISM: Artificial
<220> FEATURE:
<223> OTHER INFORMATION: Primer

```
<220> FEATURE:
<221> NAME/KEY: misc_feature
<222> LOCATION: (1)..(6)
<223> OTHER INFORMATION: n is a, c, g, or t

<400> SEQUENCE: 2
nnnnnnatag caccatggcc gatatcgtcc tgacccaga                              39

<210> SEQ ID NO 3
<211> LENGTH: 40
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(6)
<223> OTHER INFORMATION: n is a, c, g, or t

<400> SEQUENCE: 3
nnnnnntgct atcggccgcg ccacgtgcgg gtgtttatgg                             40

<210> SEQ ID NO 4
<211> LENGTH: 1062
<212> TYPE: DNA
<213> ORGANISM: Artificial
<220> FEATURE:
<223> OTHER INFORMATION: Chimeric DNA

<400> SEQUENCE: 4
gatatcgtcc tgacccagag cccggcgacc ctctcggtca cccccggcaa ctcggtgtcc       60
ctctcgtgcc gcgcctcgca gtcgatcggc aacaacctcc actggtatca gcagaagtcg      120
cacgagagcc cgcgcctcct gatcaagtac gccagccagt cgatctcggg gatcccgtcg      180
cgcttcagcg gctcgggctc gggcaccgac ttcaccctgt cgatcaacag cgtcgagacg      240
gaggacttcg gcatgtactt ctgccagcag tcgaacagct ggccgtacac cttcggcggc      300
ggtaccaagc tggagatcac cgcgggcggg ggcggtagcg gcggtggcgg gtcgggcggt      360
ggcggatcgg atatccagct gcaggagtcg ggcccgagcc tcgtcaagcc gtcgcagacc      420
ctgtcgctca cctgcagcgt caccggcgac tcgatcacct cggactactg gtcgtggatc      480
cgcaagttcc ccggcaaccg cctcgagtac atgggctacg tcagctactc gggcagcacc      540
tactacaacc cctcgctgaa gagccgcatc tcgatcaccc gcgacacctc caagaaccag      600
tactacctgg acctcaactc ggtcaccacc gaggacaccg ccacctacta ctgcgcgaac      660
tgggacggcg actactgggg ccagggcacc ctcgtcaccg tctccgccgc gggcgggggc      720
ggtagcggcg gtggcgggtc gggcggtggc ggatcgatgc acggcaaaac ccaggcgacc      780
tcaggtacca ttcagagcat gcacggtaaa acccaggcga cttcaggtac catccagtct      840
atgcatggca aaacccaggc gacttctggt accattcagt ctatgcattc agctagcggc      900
tcgggcggcg gcggctctgg tggtggttct ggtggcggct ctgagggtgg cggctctgag      960
ggaggcggtt ccggtggtgg ctctggttct attccgatgc atgtgcatca caaacacccg     1020
catgttatcc cgatgcatgt gcaccataaa cacccgcacg tg                        1062

<210> SEQ ID NO 5
<211> LENGTH: 44
<212> TYPE: PRT
<213> ORGANISM: Mus musculus
<220> FEATURE:
<221> NAME/KEY: gold-binding peptide region
<222> LOCATION: (1)..(44)
```

```
-continued

<400> SEQUENCE: 5

Met His Gly Lys Thr Gln Ala Thr Ser Gly Thr Ile Gln Ser Met His
1               5                   10                  15

Gly Lys Thr Gln Ala Thr Ser Gly Thr Ile Gln Ser Met His Gly Lys
            20                  25                  30

Thr Gln Ala Thr Ser Gly Thr Ile Gln Ser Met His
        35                  40

<210> SEQ ID NO 6
<211> LENGTH: 24
<212> TYPE: PRT
<213> ORGANISM: Mus musculus
<220> FEATURE:
<221> NAME/KEY: SiO2-binding peptide region
<222> LOCATION: (1)..(24)

<400> SEQUENCE: 6

Ile Pro Met His Val His His Lys His Pro His Val Ile Pro Met His
1               5                   10                  15

Val His His Lys His Pro His Val
            20

<210> SEQ ID NO 7
<211> LENGTH: 15
<212> TYPE: PRT
<213> ORGANISM: Artificial
<220> FEATURE:
<223> OTHER INFORMATION: Linker

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 34
<212> TYPE: PRT
<213> ORGANISM: Artificial
<220> FEATURE:
<223> OTHER INFORMATION: Linker

<400> SEQUENCE: 8

Ser Ala Ser Gly Ser Gly Gly Gly Gly Ser Gly Gly Gly Ser Gly Gly
1               5                   10                  15

Gly Ser Glu Gly Gly Gly Ser Glu Gly Gly Gly Ser Gly Gly Gly Ser
            20                  25                  30

Gly Ser
```